United States Patent
Wang et al.

(10) Patent No.: US 12,305,242 B2
(45) Date of Patent: May 20, 2025

(54) METHODS AND RELATED ASPECTS FOR QUANTITATIVE POLYMERASE CHAIN REACTION TO DETERMINE FRACTIONAL ABUNDANCE

(71) Applicants: THE JOHNS HOPKINS UNIVERSITY, Baltimore, MD (US); Pioneer Hi-Bred International, Inc., Johnston, IA (US)

(72) Inventors: Tza-Huei Jeff Wang, Timonium, MD (US); Alexander Y. Trick, Baltimore, MD (US); Xiaoyi Sopko, Wilmington, DE (US)

(73) Assignees: THE JOHNS HOPKINS UNIVERSITY, Baltimore, MD (US); PIONEER HI-BRED INTERNATIONAL, INC., Johnston, IA (US)

( * ) Notice: Subject to any disclaimer, the term of this patent is extended or adjusted under 35 U.S.C. 154(b) by 1043 days.

(21) Appl. No.: 17/239,211

(22) Filed: Apr. 23, 2021

(65) Prior Publication Data
US 2021/0340633 A1    Nov. 4, 2021

Related U.S. Application Data

(60) Provisional application No. 63/014,943, filed on Apr. 24, 2020.

(51) Int. Cl.
| | | |
|---|---|---|
| C12Q 1/68 | (2018.01) | |
| C12Q 1/6851 | (2018.01) | |
| C12Q 1/686 | (2018.01) | |
| C12Q 1/6895 | (2018.01) | |
| G16B 5/00 | (2019.01) | |
| G16B 20/20 | (2019.01) | |

(Continued)

(52) U.S. Cl.
CPC ......... *C12Q 1/6895* (2013.01); *C12Q 1/6851* (2013.01); *C12Q 1/686* (2013.01); *G16B 5/00* (2019.02); *G16B 20/20* (2019.02); *G16B 25/20* (2019.02); *G16B 40/00* (2019.02); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 7,252,976 B2 | 8/2007 | Lin et al. |
| 8,450,063 B2 | 5/2013 | Dube et al. |

(Continued)

FOREIGN PATENT DOCUMENTS

| | | |
|---|---|---|
| CA | 2603815 A1 | 10/2006 |
| WO | 2018081178 A1 | 5/2018 |

(Continued)

OTHER PUBLICATIONS

Garcia et al. (Scientific Reports, 2010, 10:17681) (Year: 2010).*

(Continued)

*Primary Examiner* — Stephanie K Mummert
(74) *Attorney, Agent, or Firm* — MH2 Technology Law Group LLP

(57) ABSTRACT

Provided herein are methods of processing grain samples to detect the fractional abundance of transgenic traits. Related systems and computer program products are also provided.

12 Claims, 17 Drawing Sheets

(51) Int. Cl.
  *G16B 25/20* (2019.01)
  *G16B 40/00* (2019.01)

(56) References Cited

U.S. PATENT DOCUMENTS

| | | | |
|---|---|---|---|
| 8,532,936 | B2 | 9/2013 | Rava |
| 8,700,341 | B2 | 4/2014 | Rava et al. |
| 9,115,401 | B2 | 8/2015 | Rava et al. |
| 9,127,312 | B2 | 9/2015 | Regan et al. |
| 9,260,745 | B2 | 2/2016 | Rava et al. |
| 9,323,888 | B2 | 4/2016 | Rava et al. |
| 9,411,937 | B2 | 8/2016 | Srinivasan et al. |
| 9,447,453 | B2 | 9/2016 | Rava et al. |
| 9,493,828 | B2 | 11/2016 | Rava et al. |
| 9,657,342 | B2 | 5/2017 | Rava et al. |
| 10,388,403 | B2 | 8/2019 | Rava et al. |
| 10,415,089 | B2 | 9/2019 | Rava et al. |
| 10,450,609 | B2 | 10/2019 | Sukumar et al. |
| 10,482,993 | B2 | 11/2019 | Rava et al. |
| 10,586,610 | B2 | 3/2020 | Rava et al. |
| 10,612,096 | B2 | 4/2020 | Rava et al. |
| 10,658,070 | B2 | 5/2020 | Rava et al. |
| 10,662,474 | B2 | 5/2020 | Rava |
| 10,704,081 | B2 | 7/2020 | Lidgard et al. |
| 2011/0177517 | A1 | 7/2011 | Rava et al. |
| 2011/0201507 | A1 | 8/2011 | Rava et al. |
| 2011/0224087 | A1 | 9/2011 | Quake et al. |
| 2011/0231132 | A1 | 9/2011 | Gunstream |
| 2015/0056191 | A1 | 2/2015 | Sathyanarayanan et al. |
| 2015/0118740 | A1 | 4/2015 | Wang et al. |
| 2018/0251848 | A1 | 9/2018 | Diehn et al. |
| 2018/0372753 | A1 | 12/2018 | Ping et al. |
| 2019/0055592 | A1 | 2/2019 | Morin et al. |
| 2019/0211391 | A1 | 7/2019 | Rabinowitz et al. |
| 2019/0250143 | A1 | 8/2019 | Zhao et al. |
| 2020/0225210 | A1 | 7/2020 | Zhao et al. |
| 2020/0385810 | A1 | 12/2020 | Rava et al. |
| 2021/0343364 | A1 | 11/2021 | Wang et al. |
| 2022/0333053 | A1 | 10/2022 | Wang et al. |

FOREIGN PATENT DOCUMENTS

| | | | |
|---|---|---|---|
| WO | 2019213096 | A1 | 11/2019 |
| WO | 2019234247 | A1 | 12/2019 |
| WO | 2020219011 | A1 | 10/2020 |
| WO | 2021243080 | A1 | 12/2021 |

OTHER PUBLICATIONS

Cerulo et al. (PLoS One, 2014, 9(1):e83235) (Year: 2014).*
Shimizu et al. (J Agric Food Chem, 2008, 56: 5521-5527) (Year: 2008).*
Pearson et al. (PLoS ONE, 2019 14 (12): e0226719, p. 1-17) (Year: 2019).*
Zhang, et al. (Anal Chem, 2018, 90:12180-12186) (Year: 2018).*
Wittman-Regis, A. (Authorized officer), International Preliminary Report on Patentability issued in corresponding International Application No. PCT/US2021/028933 mailed on Oct. 25, 2022, 7 pages.
Meyer-Kirschner, J. et al., "In-line Monitoring of Monomer and Polymer Content During Microgel Synthesis Using Precipitation Polymerization via Raman Spectroscopy and Indirect Hard Modeling." Applied Spectroscopy, 2016, vol. 70, No. 3, pp. 416-426 Abstract Only.
Kishkovich, O. (Authorized officer), International Search Report and Written Opinion in corresponding International Application No. PCT/US2021/028933 mailed on Aug. 5, 2021, 10 pages.
Meyer-Kirschner, J. et al., "In-line Monitoring of Monomer and Polymer Content During Microgel Synthesis Using Precipitation Polymerization via Raman Spectroscopy and Indirect Hard Modeling." Applied Spectroscopy, 2016, vol. 70, No. 3, pp. 416-426.
Whale et al., "Detection of Rare Drug Resistance Mutations by Digital PCR in a Human Influenza A Virus Model System and Clinical Samples", Journal of Clinical Microbiology, (Feb. 2016), vol. 54, No. 2, pp. 392-400.
Peng et al., "Development of a qualitative real-time PCR method to detect 19 targets for identification of genetically modified organisms", Springer Plus, (2016), vol. 5, No. 889, 6 pages.
Chang et al., "RMeseiacrcrho arRticNleA expression profiling to identify and validate reference genes for relative quantification in colorectal cancer", BMC Cancer, (2010), vol. 10, No. 173, 13 pages.
Puech et al., "Design and evaluation of a unique SYBR Green real-time RT-PCR assay for quantification of five major cytokines in cattle, sheep and goats", BMC Veterinary Research, (2015), vol. 11, No. 65, 14 pages.
Pfaffl., "A new mathematical model for relative quantification in real-time RT-PCR", Nucleic Acids Research, (2001), vol. 29, No. 9, 6 pages.
Ruijter et al., "Evaluation of qPCR curve analysis methods for reliable biomarker discovery: Bias, resolution, precision, and implications", Methods, (2013), vol. 59, No. 1, pp. 32-46.
Weaver et al., "Taking qPCR to a higher level: Analysis of CNV reveals the power of high throughput qPCR to enhance quantitative resolution", Methods., (2010), vol. 50, No. 4, pp. 271-276.
Sanders et al., "Evaluation of Digital PCR for Absolute DNA Quantification", Analytical Chemistry, (2011), vol. 83, No. 17, pp. 6474-6484.
Boggy, Gregory J. et al. "A mechanistic model of PCR for accurate quantification of quantitative PCR data." PloS one 5.8 (2010): e12355.
Mehra, Sarika et al. "A kinetic model of quantitative real-time polymerase chain reaction." Biotechnology and bioengineering 91.7 (2005): 848-860.
Livak, Kenneth J. et al. "Analysis of relative gene expression data using real-time quantitative PCR and the 2-$\Delta\Delta$CT method." methods 25.4 (2001): 402-408.
Sanders, Rebecca et al. "Considerations for accurate gene expression measurement by reverse transcription quantitative PCR when analysing clinical samples." Analytical and bioanalytical chemistry 406 (2014): 6471-6483.
Schweitzer et al., "Combining nucleic acid amplification and detection", 2001, Current opinion in biotechnology, vol. 12, pp. 21-27.
Vanguilder, Heather D. et al. "Twenty-five years of quantitative PCR for gene expression analysis." Biotechniques 44.5 (2008): 619-626.
Tichopad, Ales et al. "Standardized determination of real-time PCR efficiency from a single reaction set-up." Nucleic acids research 31.20 (2003): e122-e122.
Rao, Xiayu et al. "An improvement of the 2 (-delta delta CT) method for quantitative real-time polymerase chain reaction data analysis." Biostatistics, bioinformatics and biomathematics 3.3 (2013): 71.
Eisenberg, Eli et al. "Human housekeeping genes, revisited." TRENDS in Genetics 29.10 (2013): 569-574.
Zhang, Linzhong et al. "A novel data processing method CyC* for quantitative real time polymerase chain reaction minimizes cumulative error." Plos one 14.6 (2019): e0218159.
Chervoneva et al., "Modeling qRT-PCR dynamics with application to cancer biomarker quantification", 2018, Statistical methods in medical research, vol. 27, No. 9, pp. 2581-2595.
Zhang, Ye et al. "Ratiometric fluorescence coding for multiplex nucleic acid amplification testing." Analytical chemistry 90.20 (2018): 12180-12186.

* cited by examiner

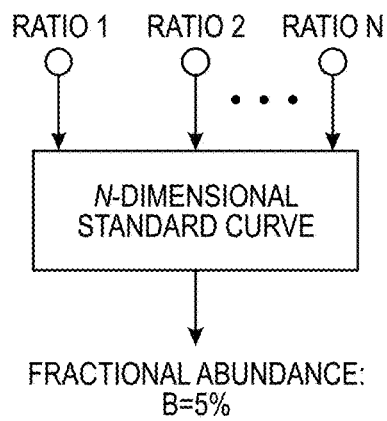

FIG. 1C

```
200 ─┐
  202 ─┐
  ┌─────────────────────────────────────────────────────────────────────┐
  │ AMPLIFYING A FIRST TARGET NUCLEIC ACID AND A FIRST REFERENCE NUCLEIC ACID │
  │ TOGETHER IN A REACTION MIXTURE TO PRODUCE RATIOMETRIC DATA THAT INCLUDES │
  │ RATIOS OF DETECTABLE SIGNAL LEVELS DETECTED AS THE FIRST TARGET NUCLEIC │
  │     ACID AND THE FIRST REFERENCE NUCLEIC ACID ARE AMPLIFIED         │
  └─────────────────────────────────────────────────────────────────────┘
                                    │
  204 ─┐                             ▼
  ┌─────────────────────────────────────────────────────────────────────┐
  │ APPLYING A RATIOMETRIC REGRESSION ALGORITHM TO THE RATIOMETRIC DATA TO │
  │ DETERMINE THE FRACTIONAL ABUNDANCE OF THE TARGET VARIANT IN THE POPULATION │
  └─────────────────────────────────────────────────────────────────────┘
```

FIG. 2

METHODS AND RELATED ASPECTS FOR QUANTITATIVE POLYMERASE CHAIN REACTION TO DETERMINE FRACTIONAL ABUNDANCE

CROSS-REFERENCE TO RELATED APPLICATIONS

This application claims priority to U.S. Provisional Patent Application Ser. Nos. 63/014,943, filed Apr. 24, 2020, the disclosure of which is incorporated herein by reference.

STATEMENT REGARDING FEDERALLY SPONSORED RESEARCH OR DEVELOPMENT

This invention was made with government support under AI138978 awarded by the National Institutes of Health. The government has certain rights in the invention.

BACKGROUND

Assessment of relative gene expression has broad applications in a variety of research and industry settings. Agroscience companies use high resolution quantification to monitor usage of their products in farms [Peng et al., "Development of a qualitative real-time PCR method to detect 19 targets for identification of genetically modified organisms," *Springerplus*, vol. 5, no. 1, 2016]. Molecular biologists use relative gene expression to assess cell responses to experimental conditions such as drug exposure or diagnosis diseases like cancer [Chang et al., "MicroRNA expression profiling to identify and validate reference genes for relative quantification in colorectal cancer," *BMC Cancer*, vol. 10, 2010]. Veterinarians may use gene expression to monitor the disease states of livestock [Puech et al., "Design and evaluation of a unique SYBR Green real-time RT-PCR assay for quantification of five major cytokines in cattle, sheep and goats," *BMC Vet. Res.*, vol. 11, no. 1, p. 65, 2015]. Most quantification of genes is carried out today with traditional quantitative polymerase chain reaction (qPCR) wherein real-time fluorescence of separate reactions for amplifying a reference gene and a target gene respectively are compared to assess fractional abundance (FA) of the target gene [Pfaffl, "A new mathematical model for relative quantification in real-time RT-PCR," Nucleic Acids Res., vol. 29, no. 9, pp. 45e-45, May 2001].

Use of standard qPCR methods is suitable for detecting orders of magnitude differences in genetic expression, but distinguishing changes smaller than 2-fold is unreliable [Ruijter et al., "Evaluation of qPCR curve analysis methods for reliable biomarker discovery: Bias, resolution, precision, and implications," *Methods*, vol. 59, no. 1, pp. 32-46, 2013]. Resolution of qPCR can be improved with higher throughput assays with many replicates, though this can be prohibitively laborious or expensive for practical use [Weaver et al., "Taking qPCR to a higher level: Analysis of CNV reveals the power of high throughput qPCR to enhance quantitative resolution," *Methods*, vol. 50, no. 4, pp. 271-276, 2010]. Alternative methods that digitize samples such as droplet digital PCR or digital array chips can produce higher resolution by counting the presence of individual strands of DNA, but such platforms are limited in dynamic range and require sophisticated instrumentation [Sanders et al., "Evaluation of digital PCR for absolute DNA quantification," *Anal. Chem.*, vol. 83, no. 17, pp. 6474-6484, 2011].

Accordingly, there is a need for additional methods, and related aspects, for high-resolution quantitative real-time polymerase chain reaction (qPCR).

SUMMARY

The present disclosure relates, in certain aspects, to methods, systems, and computer readable media of use in processing grain samples to detect the fractional abundance of transgenic traits in those samples. These and other aspects will be apparent upon a complete review of the present disclosure, including the accompanying figures.

In some aspects, the present disclosure provides a method of processing a grain sample to detect the fractional abundance of a transgenic trait. The method includes grinding and mixing the grain sample, and extracting and purifying DNA from the grain sample. The method also includes running said purified DNA sample in a qPCR reaction, said qPCR reaction comprising at least two different fluorescent probes that competitively bind to the same DNA locus, wherein said DNA locus is indicative of the presence or absence of a transgenic trait. In addition, the method also includes generating results of the qPCR reaction that characterize the competitive binding levels of each of the at least two different fluorescent probes during each cycle of the qPCR reaction, and interpreting said results with one or more of a machine learning model, ratiometric regression algorithm, or best fit model to determine the fractional abundance of the transgenic trait. In some embodiments, the method uses multivariate parabolic weighted regression.

In some embodiments of the methods disclosed herein, the results of the qPCR reaction that characterize the competitive binding levels of each of the at least two different fluorescent probes during each cycle of the qPCR reaction are at least one of a standard curve or an N-dimensional curve. In some embodiments of the methods disclosed herein, a machine learning model is used, and the machine learning model has been trained on a range of grain samples comprising levels from 0-100% of transgenic grain in increments of 30% less. In some embodiments of the methods disclosed herein, a machine learning model is used, and the machine learning model has been trained on a range of grain samples comprising levels from 0-100% of transgenic grain in 10% increments. In some embodiments of the methods disclosed herein, a machine learning model is used, and the machine learning model has been trained on a range of grain samples comprising levels from 0-100% of transgenic grain in 5% increments. In some of these embodiments, the machine learning model is a support vector machine model. In some of these embodiments, the results of the qPCR reaction input into the support vector machine model comprise the ratio of the fluorescence values of FAM/(FAM+VIC).

In certain embodiments of the methods disclosed herein, the transgenic trait is glyphosate resistance, and the method identifies the genetic sequence that confers glyphosate resistance. In some embodiments of the methods disclosed herein, the at least two different fluorescent probes are FAM and VIC. In some of these embodiments, the results of the qPCR reaction input into the support vector machine model comprise the ratio of the fluorescence values of FAM/(FAM+VIC). In some embodiments of the methods disclosed herein, the time elapsed from processing the grain sample to detecting the fractional abundance of the transgenic trait is 15 minutes or less. In some embodiments of the methods disclosed herein, the grain is soybean, corn, sunflower, wheat or canola.

BRIEF DESCRIPTION OF THE DRAWINGS

The accompanying drawings, which are incorporated in and constitute a part of this specification, illustrate certain embodiments, and together with the written description, serve to explain certain principles of the methods, devices, kits, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIGS. 1A-C schematically shows an overview of a quantitative ratiometric regression PCR (qRR-PCR) method according to some exemplary embodiments. In particular, FIG. 1A is a plot of a duplexed (Genes A and B) real-time qRR-PCR in which fluorescence (A.U.) is represented on the y-axis and the cycle number is represented on the x-axis. FIG. 1B is a plot of fluorescence ratios of Gene A over the cumulative fluorescence in which fluorescence ratios (FAM/FAM+VIC) are represented on the y-axis and the cycle number is represented on the x-axis. FIG. 1C schematically depicts fluorescence ratios being fed into an N-dimensional standard curve to yield an estimate of the fractional abundance (FA) of Gene B. As shown, for each gene or other target nucleic acid of interest, a standard curve is created from data generated in multiplexed PCR reactions containing a known composition of reference and target genes.

FIG. 2 is a flow chart that schematically shows exemplary method steps of determining a fractional abundance of a target variant in a population according to some aspects disclosed herein.

FIGS. 7 A and B are plots showing data conversion to ratiometric curves according to one exemplary embodiment. As shown.

FIGS. 9A-C represent the same curve and data with varying rotations to show the tight fit of the raw data (points) onto the curve.

FIGS. 10 A and B are plots showing qRR-PCR resolution and the effect of sampling size. A sampling simulation was run for 100 trials at each fractional abundance with either 1, 3, or 5 samples selected in each trial with replacement.

DEFINITIONS

Figure 1A:
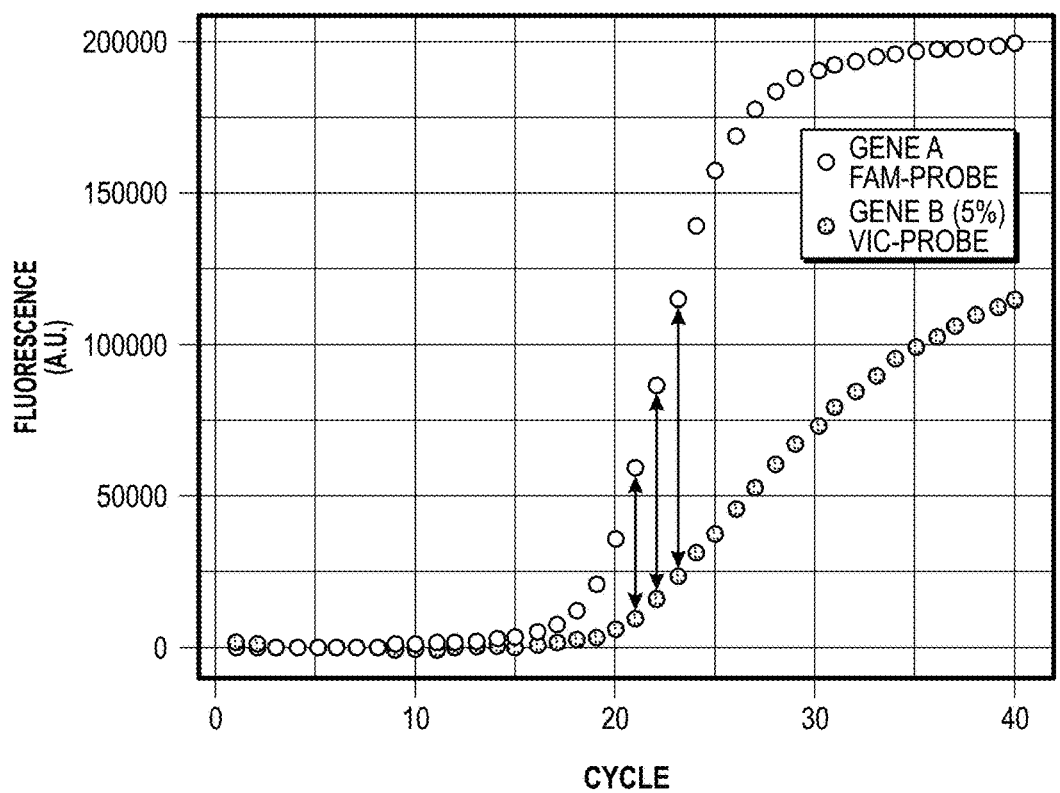

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, systems, computer readable media, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Administering: As used herein, the terms "administering" and "administration" refer to any method of providing a pharmaceutical preparation or other treatment to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

Amplifying: As used herein, "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using RT-PCR is a form of amplification. Furthermore, the generation of multiple RNA molecules from a single DNA molecule during the process of transcription is also a form of amplification.

Baseline Detectable Signal: As used herein, "baseline detectable signal" in the context of an amplification reaction refers to detectable signal emitted in a given detection system prior to the quantitation cycle (Ct).

Detect: As used herein, "detect," "detecting," or "detection" refers to an act of determining the existence or presence of one or more target nucleic acids (e.g., nucleic acids having targeted mutations or other markers) in a sample.

Detectable Signal: As used herein, "detectable signal" refers to signal output at an intensity or power sufficient to be detected in a given detection system. In certain embodiments, a detectable signal is emitted from a label (e.g., a fluorescent label or the like) associated with a given primer nucleic acid and/or probe nucleic acid.

Exonuclease Probe: As used herein, "exonuclease probe" refers to a labeled oligonucleotide that is capable of producing a detectable signal change upon being cleaved. To illustrate, in certain embodiments an exonuclease probe is a 5'-nuclease probe comprising two labeling moieties and emits radiation of increased intensity after one of the labels is cleaved or otherwise separated from the oligonucleotide. In some of these embodiments, for example, the 5'-nuclease probe is labeled with a 5' terminus quencher moiety and a reporter moiety at the 3' terminus of the probe. In certain embodiments, 5'-nuclease probes are labeled at one or more positions other than, or in addition to, these terminal positions. When the probe is intact, energy transfer typically occurs between the labeling moieties such that the quencher moiety at least in part quenches the fluorescent emission from the acceptor moiety. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission from the acceptor moiety is no longer quenched. To further illustrate, in certain embodiments 5'-nuclease probes include regions of self-complementarity such that the probes are capable of forming hairpin structures under selected conditions. In these embodiments, 5'-nuclease probes are also referred to herein as "hairpin probes."

Fractional Abundance: As used herein, "fractional abundance" refers to the proportion or percentage frequency of one component (e.g. a target nucleic acid) relative to another component(s) (e.g., a reference nucleic acid and/or other components of a reaction mixture or other composition that includes the target nucleic acid).

Hairpin Probe: As used herein, "hairpin probe" refers to an oligonucleotide that can be used to effect target nucleic acid detection and that includes at least one region of self-complementarity such that the probe is capable of forming a hairpin or loop structure under selected conditions. Typically, hairpin probes include one or more labeling moieties. In one exemplary embodiment, quencher moieties and reporter moieties are positioned relative to one another in the hairpin probes such that the quencher moieties at least partially quench light emissions from the reporter moieties when the probes are in hairpin confirmations. In contrast, when the probes in these embodiments are not in hairpin confirmations (e.g., when the probes are hybridized with target nucleic acids), light emissions the acceptor reporter moieties are generally detectable. Hairpin probes are also known as molecular beacons in some of these embodiments. Hairpin probes can also function as 5'-nuclease probes or hybridization probes in certain embodiments.

Hybridization Probe: As used herein, "hybridization probe" refers an oligonucleotide that includes at least one labeling moiety that can be used to effect target nucleic acid detection. In some embodiments, hybridization probes function in pairs. In some of these embodiments, for example, a first hybridization probe of a pair includes at least one donor moiety at or proximal to its 3'-end, while the second hybridization probe of the pair includes at least one acceptor moiety (e.g., LC-Red 610, LC-Red 640, LC-Red 670, LC-Red 705, JA-270, CY5, or CY5.5) at or proximal to its 5'-end. The probes are typically designed such that when both probes hybridize with a target or template nucleic acid (e.g., during a PCR), the first hybridization probe binds to the 5'-end side or upstream from the second hybridization probe and within sufficient proximity for energy transfer to occur between the donor and acceptor moieties to thereby produce a detectable signal. Typically, the second hybridization probe also includes a phosphate or other group on its 3'-end to prevent extension of the probe during a PCR.

Label: As used herein, "label" refers to a moiety attached (covalently or non-covalently), or capable of being attached, to a molecule, which moiety provides or is capable of providing information about the molecule (e.g., descriptive, identifying, etc. information about the molecule). Exemplary labels include donor moieties, acceptor moieties, fluorescent labels, non-fluorescent labels, calorimetric labels, chemiluminescent labels, bioluminescent labels, radioactive labels, mass-modifying groups, antibodies, antigens, biotin, haptens, and enzymes (including, e.g., peroxidase, phosphatase, etc.).

Logistic Regression: As used herein, "logistic regression" refers to a statistical model use to examine and describe the relationship between a binary response variable and a set of predictor variables.

Machine Learning Algorithm: As used herein, "machine learning algorithm" generally refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fisher's analysis), support vector machines (SVMs), decision trees (e.g., recursive partitioning processes such as CART—classification and regression trees, or random forests), linear classifiers (e.g., multiple linear regression (MLR), partial least squares (PLS) regression, and principal components regression), hierarchical clustering, and cluster analysis. A dataset on which a machine learning algorithm learns can be referred to as "training data." A model produced using a machine learning algorithm is generally referred to herein as a "machine learning model."

Mixture: As used herein, "mixture" refers to a combination of two or more different components.

Nucleic Acid: As used herein, "nucleic acid" refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., bromodeoxyuridine (BrdU)), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA, cfDNA, ctDNA, or any combination thereof.

Primer Nucleic Acid: As used herein, "primer nucleic acid" or "primer" refers to a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide). Although other primer nucleic acid lengths are optionally utilized, they typically comprise hybridizing regions that range from about 8 to about 100 nucleotides in length. Short primer nucleic acids generally require cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include donor moieties, acceptor moieties, quencher moieties, radioisotopes, electron-dense reagents, enzymes (as commonly used in performing ELISAs), biotin, or haptens and proteins for which antisera or monoclonal antibodies are available. Many of these and other labels are described further herein and/or are otherwise known in the art. One of skill in the art will recognize that, in certain embodiments, primer nucleic acids can also be used as probe nucleic acids.

Probe Nucleic Acid: As used herein, "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using a probe under sufficiently stringent hybridization conditions permits the selective detection of a specific target sequence. The term "hybridizing region" refers to that region of a nucleic acid that is exactly or substantially complementary to, and therefore capable of hybridizing to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support. A probe of the invention is generally included in a nucleic acid that comprises one or more labels (e.g., donor moieties, acceptor moieties, and/or quencher moieties), such as exonuclease probe (e.g., a 5'-nuclease probe), a hybridization probe, a fluorescent resonance energy transfer (FRET) probe, a hairpin probe, or a molecular beacon, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable hybridization complexes may contain mismatched bases or unmatched bases. Modification of the stringent conditions may be necessary to permit a stable hybridization complex with one or more base pair mismatches or unmatched bases. Stability of the target/probe hybridization complex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

Quantitation Cycle: As used herein, "quantitation cycle," "Cq," "cycle threshold," or "Ct" refers to the cycle or point in a given amplification reaction at which the detectable signal intensity or power is above background noise levels.

Reaction Mixture: As used herein, "reaction mixture" refers to a mixture that comprises molecules that can participate in and/or facilitate a given reaction or assay. To illustrate, an amplification reaction mixture generally includes a solution containing reagents necessary to carry out an amplification reaction, and typically contains primers, a biocatalyst (e.g., a nucleic acid polymerase, a ligase, etc.), dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components.

Reference: As used herein, "reference" in the context of a nucleic acid refers to a known sequence used for purposes of comparison with experimentally determined or test sequences. For example, a known sequence can be an entire genome, a chromosome, or any segment thereof. A reference sequence typically includes at least about 20, at least about 50, at least about 100, at least about 200, at least about 250, at least about 300, at least about 350, at least about 400, at least about 450, at least about 500, at least about 1000, at least about 100000, at least about 1000000, at least about 1000000000, or more nucleotides. A reference sequence can align with a single contiguous sequence of a genome or chromosome or can include non-contiguous segments that align with different regions of a genome or chromosome. Exemplary reference sequences, include, for example, human genomes, such as, hG19 and hG38.

Residual Sum of Squares: As used herein, "residual sum of squares" or "RSS" refers to a statistical technique used to measure the amount of variance in a data set that is not explained by a regression model.

Sample: As used herein, "sample" refers to a tissue or organ from a subject; a cell (either within a subject, taken directly from a subject, or a cell maintained in culture or from a cultured cell line); a ceil lysate (or lysate fraction) or cell extract; or a solution containing one or more molecules derived from a cell or cellular material (e.g., a nucleic acid), which is assayed as described herein. A sample may also be any body fluid or excretion (for example, but not limited to, blood, urine, stool, saliva, tears, bile) that contains cells, cell components, or non-cellular fractions.

Subject: As used herein, "subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject." For example, a subject can be an individual who has been diagnosed with having a respiratory disease, disorder, or condition, is going to receive a therapy for a respiratory disease, disorder, or condition, and/or has received at least one therapy for a respiratory disease, disorder, or condition.

System: As used herein, "system" in the context of analytical instrumentation refers a group of objects and/or devices that form a network for performing a desired objective.

Target: As used herein, "target" refers to a biomolecule (e.g., a nucleic acid, etc.), or portion thereof, that is to be amplified, detected, and/or otherwise analyzed.

Treatment: As used herein, "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human.

Value: As used herein, "value" generally refers to an entry in a dataset that can be anything that characterizes the feature to which the value refers. This includes, without limitation, numbers, words or phrases, symbols (e.g., + or −) or degrees.

DETAILED DESCRIPTION

Quantification of genetic traits has broad applications for diagnostics and quality control in research and industry settings of agriculture, livestock, and healthcare. Current methods for quantification are limited in either resolution or complexity of instrumentation and execution. The present disclosure provides methods, systems, computer readable media, and related aspects for computing relative fractional abundance of genetic traits with, for example, less than about 5% resolution from a single duplexed or higher level multiplexed real-time quantitative polymerase chain reaction (PCR) assay.

By using traditional qPCR instrumentation coupled with multiplexed PCR assays and associated analysis algorithms, the present disclosure provides for the relative quantification for fractional abundance (FA) determination with a resolution of about 5% or less. While traditional qPCR uses a single point for each gene or other target nucleic acid separately to determine quantification, the present disclosure relates in certain aspects to a quantitative ratiometric regression PCR (qRR-PCR) algorithm that leverages direct comparisons of multiple data points to improve the precision in FA calculations. These and other aspects will be apparent upon a complete review of the present disclosure.

Exemplary Methods

Figure 1B:
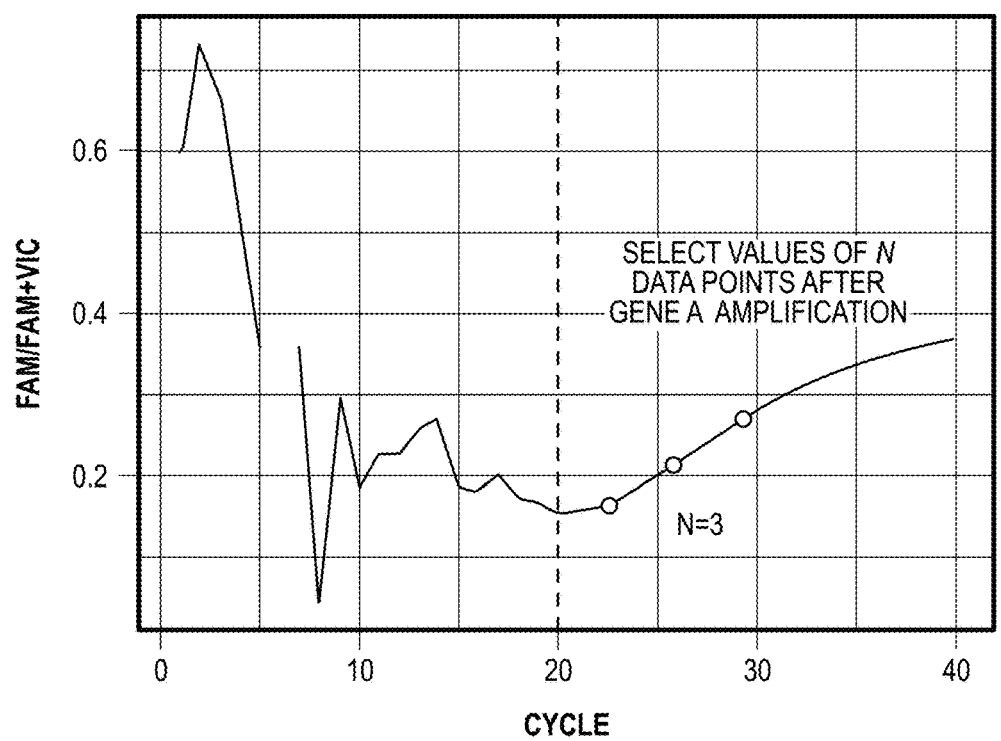

To illustrate, FIGS. 1A-C schematically depict an overview of a quantitative ratiometric regression PCR (qRR- PCR) method according to some exemplary embodiments. As shown, FIG. 1A shows a plot of a qPCR in which two genes are amplified in a single reaction. Gene A is amplified using a FAM labeled fluorescent probe (e.g., an exonuclease probe, a hairpin probe, a hybridization probe, or the like) and represents the target nucleic acid. Gene B is amplified using a VIC labeled fluorescent probe (e.g., an exonuclease probe, a hairpin probe, a hybridization probe, or the like) that is present in the reaction mixture at 5% fractional abundance. The ratios at each cycle after amplification of Gene A is calculated (indicated for 3 of the cycles by the vertical blue arrows). FIG. 1B shows a plot of fluorescence ratios of Gene A (FAM) over the cumulative fluorescence (FAM+VIC) plotted with a vertical dashed line indicating the quantitation cycle (Cq) value determined for Gene A. Subsequent analysis is conducted using data points from multiple cycles after the dashed line. FIG. 1C shows that fluorescence ratios are fed into a standard curve generated algorithmically from calibration data with known fractional abundance to yield an estimate for the fractional abundance of Gene B. Exemplary approaches to generating standard curves are described further herein.

To further illustrate, FIG. 2 is a flow chart that schematically shows exemplary method steps of determining a fractional abundance of a target variant (e.g., a genetic locus, a genome, a cell type, an organism, or the like) in a population according to some aspects disclosed herein. As shown, method 200 includes amplifying a first target nucleic acid (e.g., a target nucleic acid that includes a genetic locus of interest) and a first reference nucleic acid together in a reaction mixture (e.g., together in a reaction mixture that is disposed in the same well of a microwell plate, on a solid support, or in or on another type of reaction substrate, vessel, or container) to produce ratiometric data that includes ratios of detectable signal levels detected as (e.g., in substantially real-time) the first target nucleic acid and the first reference nucleic acid are amplified (step 202). Essentially any nucleic acid that differs from the target nucleic acid is optionally utilized as the reference nucleic acid. Method 200 also includes applying a ratiometric regression algorithm, as described herein, to the ratiometric data to determine the fractional abundance of the target variant in the population (step 204).

Figure 3:
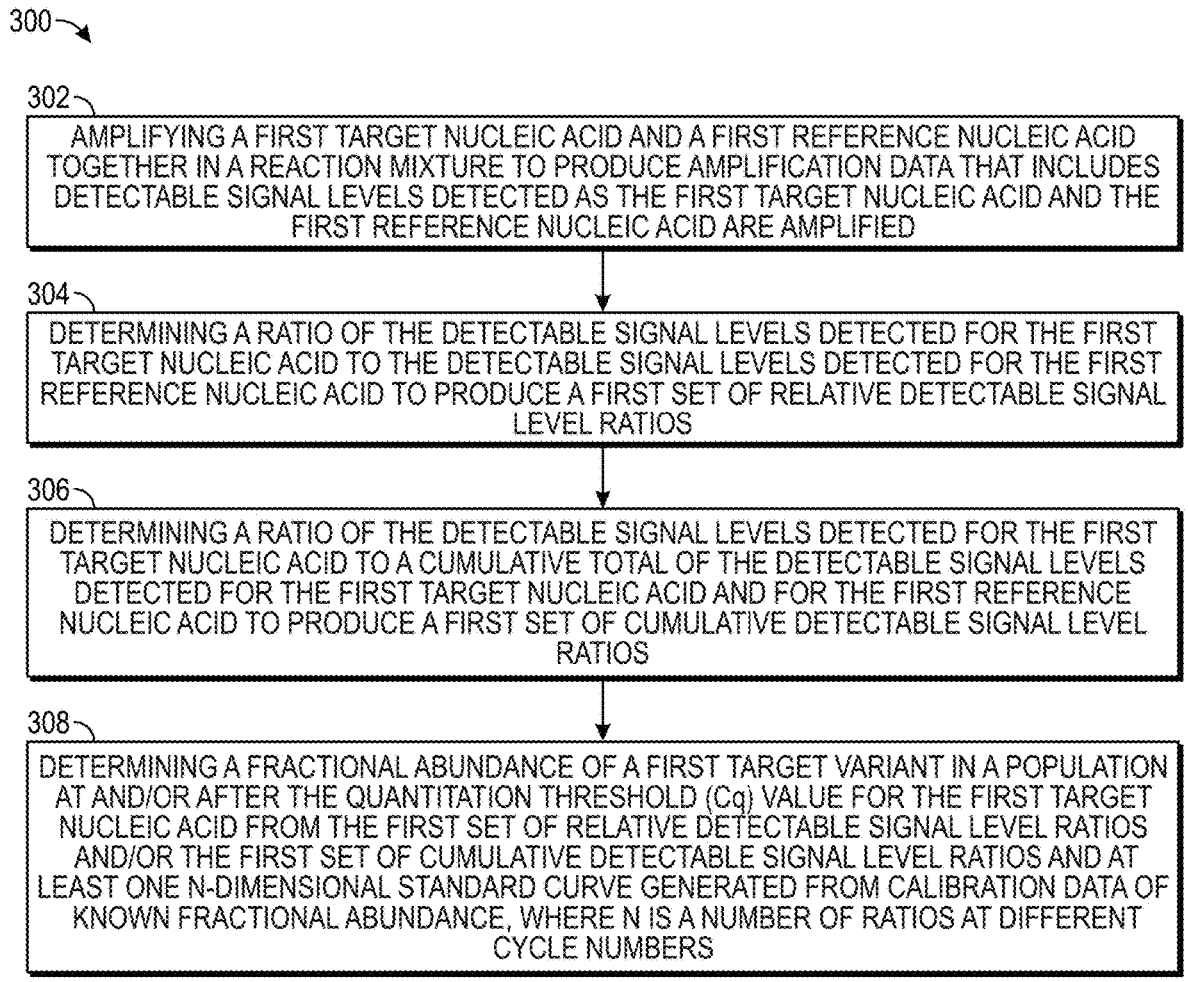
FIG. 3 is a flow chart that schematically shows exemplary method steps of determining a fractional abundance of a target variant in a population according to some aspects disclosed herein.

As an additional example, FIG. 3 is a flow chart that schematically shows exemplary method steps of determining a fractional abundance of a target variant in a population according to some aspects disclosed herein. As shown, method 300 includes amplifying a first target nucleic acid and a first reference nucleic acid together in a reaction mixture to produce amplification data that includes detectable signal levels detected as (e.g., in substantially real-time) the first target nucleic acid and the first reference nucleic acid are amplified (step 302). Method 300 also includes determining a ratio of the detectable signal levels detected for the first target nucleic acid to the detectable signal levels detected for the first reference nucleic acid to produce a first set of relative detectable signal level ratios (step 304). Method 300 further includes determining a ratio of the detectable signal levels detected for the first target nucleic acid to a cumulative total of the detectable signal levels detected for the first target nucleic acid and for the first reference nucleic acid to produce a first set of cumulative detectable signal level ratios (step 306). In addition, method 300 also includes determining a fractional abundance of the first target variant in the population at and/or after the quantitation threshold (Cq) value for the first target nucleic acid from the first set of relative detectable signal level ratios and/or the first set of cumulative detectable signal level ratios and at least one N-dimensional standard curve generated from calibration data of known fractional abundance, where N is a number of ratios at different cycle numbers (step 308).

In some embodiments, the N-dimensional standard curve generated by: amplifying a first target nucleic acid and a first reference nucleic acid together in the reaction mixture to produce amplification data that comprises one or more detectable signal levels detected as the first target nucleic acid and the first reference nucleic acid are amplified in which at least initial fractional abundances of the first target nucleic acid and the first reference nucleic acid in the reaction mixture are known. These methods also typically include subtracting at least one baseline detectable signal level value (e.g., a minimum detectable signal level value, etc.) from the amplification data to produce baseline adjusted data, and determining one or more ratios from the baseline adjusted data at one or more amplification cycles to produce at least a first set of amplification ratios. These methods also generally include calculating adjusted cycle numbers for the first set of amplification ratios to produce at least a first set of adjusted amplification data, fitting fractional abundance values to the first set of adjusted amplification data using at least one fitting technique to produce fractional abundance fits, and selecting a best fit for modeling fractional abundance from the fractional abundance fits. Additional exemplary methods of generating standard curves are described herein.

In certain embodiments, the methods disclosed herein include determining a fractional abundance of more than one target variant (e.g., about 2, about 3, about 4, about 5, about 6, about 7, about 8, about 9, about 10, or more target variants) in a given reaction mixture. In some embodiments, the detectable signal levels comprise fluorescence signals, although essentially any other detectable signal that can be generated in a real-time PCR is optionally used. In certain embodiments, the methods include amplifying the first target nucleic acid and the first reference nucleic acid together in the reaction mixture using fluorescently labeled real-time nucleic acid primers (e.g., Scorpion® primers, etc.) and/or fluorescently labeled real-time nucleic acid probes (e.g., exonuclease probes (e.g., 5'-nuclease probes or TaqMan® probes), hairpin probes, hybridization probes, etc.).

In some embodiments, the methods include determining the ratio of the detectable signal levels detected for the first target nucleic acid to the detectable signal levels detected for the first reference nucleic acid at each of the amplification cycles to produce the first set of relative detectable signal level ratios. In certain embodiments, the methods include determining the ratio of the detectable signal levels detected for the first target nucleic acid to the cumulative total of the detectable signal levels detected for the first target nucleic acid and for the first reference nucleic acid at each amplification cycle to produce the first set of cumulative detectable signal level ratios. In certain embodiments, the methods include determining the ratio of the detectable signal level detected for the first target nucleic acid to the detectable signal level detected for the first reference nucleic acid after an elongation step of a given amplification cycle.

In certain embodiments, the first target nucleic acid comprises at least a portion of at least one target genetic locus (e.g., a gene, an exon, an intron, a splice variant, etc.). In some of these embodiments, the target genetic locus is associated with at least one disease, condition, or disorder (e.g., an etiological agent, a cancer type, a cardiovascular disease, or a genetic disorder, among many others). In certain embodiments, the methods include obtaining the first target nucleic acid from a subject (e.g., from a blood or tissue sample obtained from the subject). In some of these embodiments, the fractional abundance of the target nucleic acid in the reaction mixture indicates that the subject has the disease, condition, or disorder. In certain of these embodiments, the methods include administering one or more therapies to the subject to treat the disease, condition, or disorder in the subject.

Figure 4:
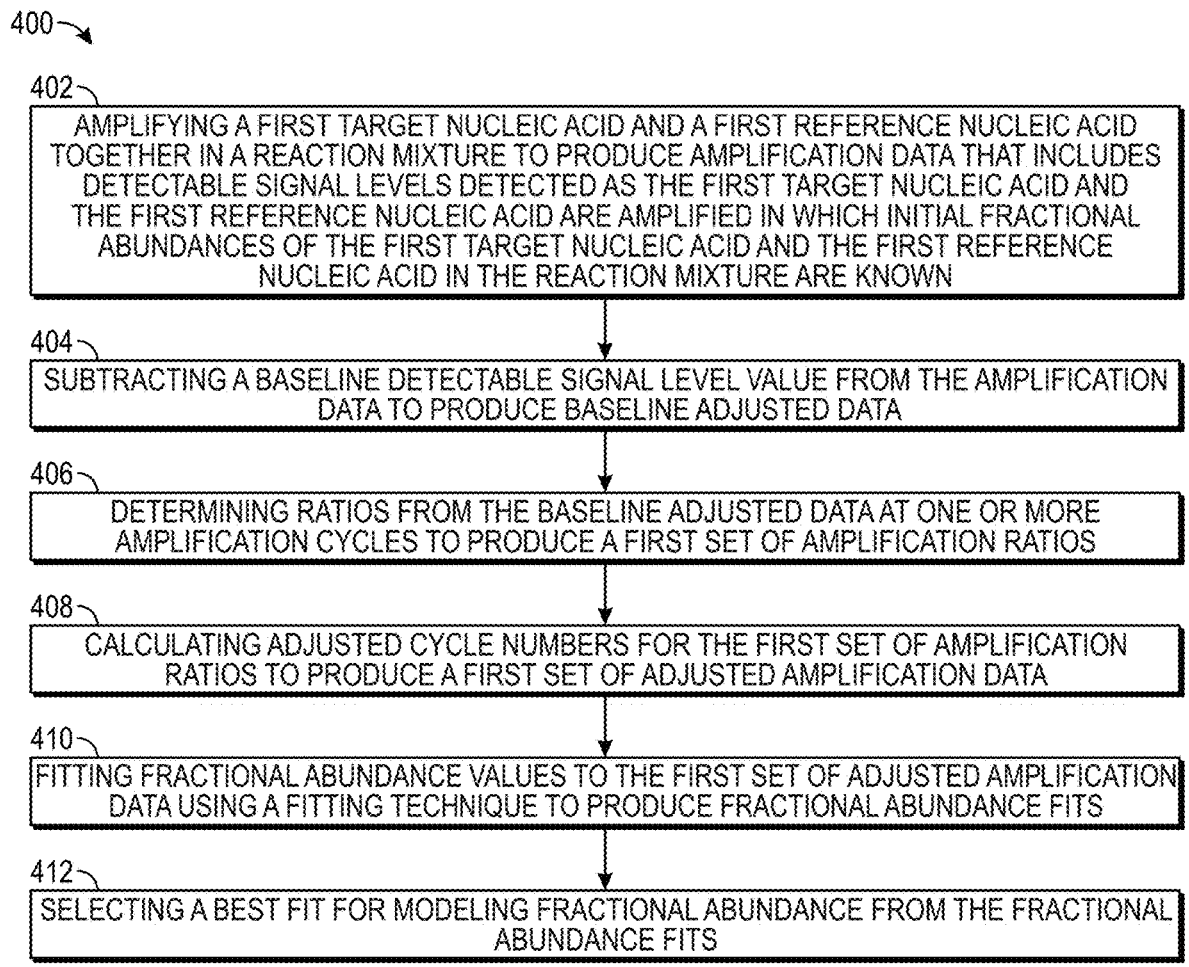
FIG. 4 is a flow chart that schematically shows exemplary method steps of generating a standard curve for determining a fractional abundance of a target variant in a population according to some aspects disclosed herein.
Figure 5:
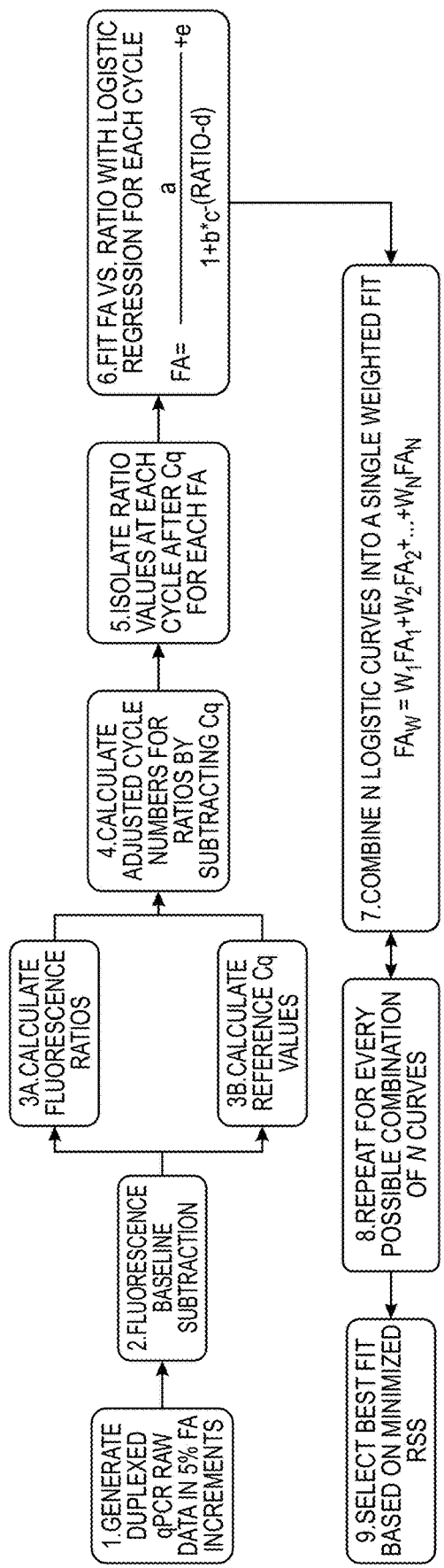
FIG. 5 is a flow chart that schematically shows exemplary method steps associated with a standard curve generation algorithm according to some aspects disclosed herein.

Various approaches for generating standard curves of use in the methods described herein are optionally utilized. As but one example, FIG. 4 is a flow chart that schematically shows exemplary method steps of generating a standard curve for determining a fractional abundance of a target variant in a population according to some aspects disclosed herein. As shown, method 400 includes amplifying a first target nucleic acid and a first reference nucleic acid together in a reaction mixture to produce amplification data that includes detectable signal levels detected as the first target nucleic acid and the first reference nucleic acid are amplified in which initial fractional abundances of the first target nucleic acid and the first reference nucleic acid in the reaction mixture are known (step 402). Method 400 also includes subtracting a baseline detectable signal level value (e.g., a minimum detectable signal level value, etc.) from the amplification data to produce baseline adjusted data (step 404) and determining ratios from the baseline adjusted data at one or more amplification cycles to produce a first set of amplification ratios (step 406). As additionally shown, method 400 further includes calculating adjusted cycle numbers for the first set of amplification ratios to produce a first set of adjusted amplification data (step 408), fitting fractional abundance values to the first set of adjusted amplification data using at least one fitting technique to produce fractional abundance fits (step 410), and selecting a best fit for modeling fractional abundance from the fractional abundance fits (step 412). As another example, the overall algorithm workflow of data generation, processing, and regression is schematically outlined in FIG. 5, which is also described further herein.

In some embodiments, the methods include generating the standard curve for determining the fractional abundance of the target variant in the population using multiple different known initial fractional abundances of the first target nucleic acid and the first reference nucleic acid in the reaction mixture. In certain embodiments, the initial fractional abundance of the first reference nucleic acid in the reaction mixture is about 5%. Other initial fractional abundances of the first reference nucleic acid in a given reaction mixture are also optionally utilized (e.g. less than about 5% (e.g., about 1%, about 2%, about 3%, or about 4%) or more than about 5% (e.g., about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%).

In some embodiments, the methods disclosed herein include selecting the best fit for modeling fractional abundance using a residual sum of squares (RSS) technique. In certain embodiments, the methods include calculating the adjusted cycle numbers by subtracting a nearest integer value to a quantitation cycle (Cq) value for the first reference nucleic acid. In some embodiments, the methods include determining a quantitation cycle (Cq) value for the first target nucleic acid and/or the first reference nucleic acid from the amplification data. In certain embodiments, the methods include determining the cumulative detectable signal ratio at a given amplification cycle using equation (1A):

$$DS_{ratio} = \frac{DS_{1stTNA}}{DS_{1stTNA} + DS_{1stRNA}} \tag{1A}$$

where $DS_{ratio}$ is the cumulative detectable signal ratio at the given amplification cycle, $DS_{1st\ TNA}$ is a baseline subtracted detectable signal value detected for the first target nucleic acid at the given amplification cycle, and $DS_{1st\ RNA}$ is a baseline subtracted detectable signal value detected for the first reference nucleic acid at the given amplification cycle. In some embodiments, the methods include performing univariate logistic regression by fitting a fractional abundance value to a cumulative detectable signal ratio for a given amplification cycle to produce at least one univariate fit using equation (2A):

$$FA = \frac{a}{1 + b * c^{-(R(x)-d)}} + e \tag{2A}$$

where FA is the predicted FA, R is the cumulative detectable signal ratio at the given cycle, x, and a, b, c, d, and, e are constants.

In certain embodiments, the methods disclosed herein include fitting the fractional abundance value to one or more cycles after the reference Cq value. In some embodiments, the methods include performing bivariate weighted regression by fitting one or more pairs of the univariate logistic regressions to the cumulative detectable signal ratios with parabolic weighting to produce at least one bivariate fit. In some of these embodiments, the methods include determining the best fit for modeling fractional abundance by calculating a residual sum of squares (RSS) for the univariate and bivariate fits and selecting a model with a lowest RSS value. In certain embodiments, the methods include identifying ratio values in the first set of adjusted amplification data that are at and/or after a quantitation cycle (Cq) value to produce at least a first set of selected reference Cq values. In certain embodiments, the methods include subtracting a quantitation cycle (Cq) value for the first reference nucleic acid from the first set of amplification ratios to produce at least a first set of adjusted amplification data.

Figure 11:
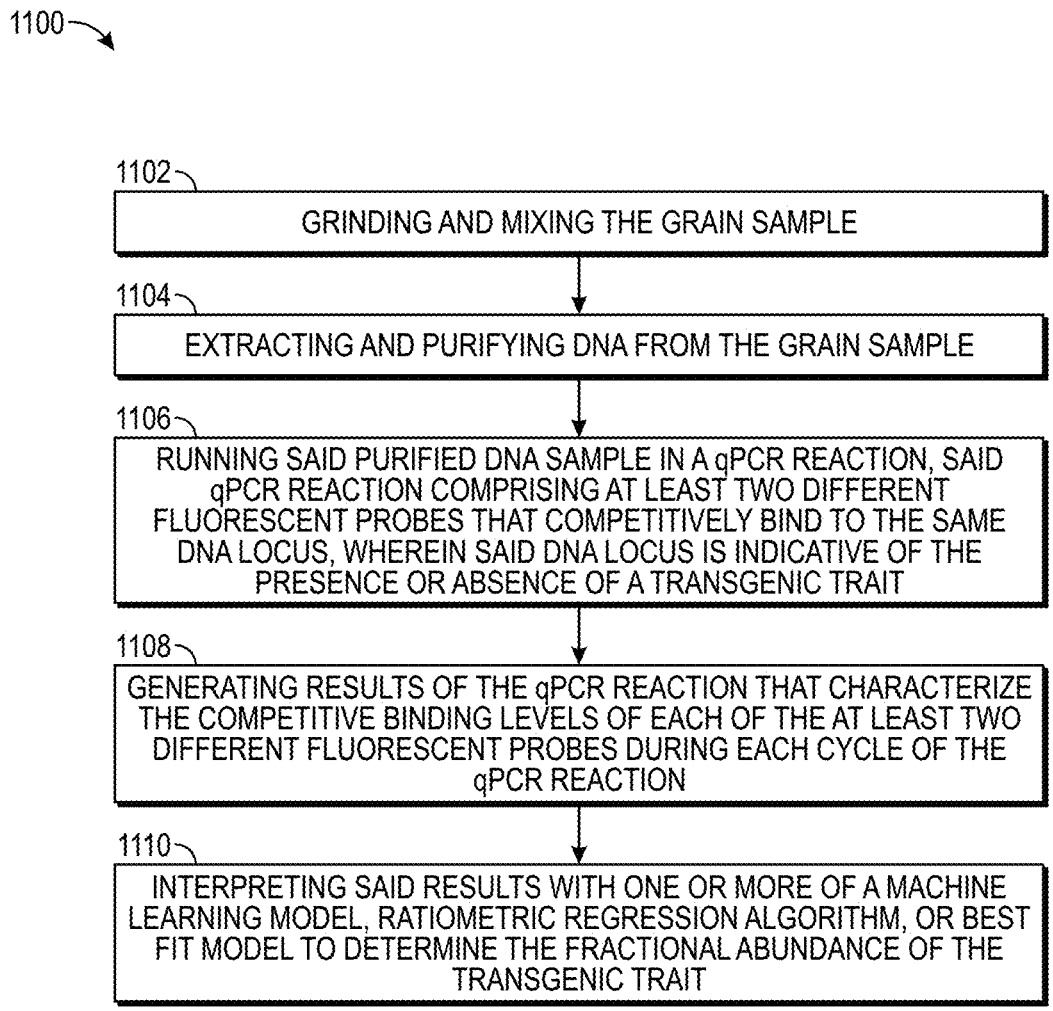
FIG. 11 is a flow chart that schematically shows exemplary method steps of processing a grain sample to detect the fractional abundance of a transgenic trait according to some aspects disclosed herein.

To further illustrate, FIG. 11 is a flow chart that schematically shows exemplary method steps of processing a grain sample (e.g., soybean, corn, sunflower, wheat, canola, or the like) to detect the fractional abundance of a transgenic trait according to some aspects disclosed herein. As shown, method 1100 includes grinding and mixing the grain sample (step 1102), and extracting and purifying DNA from the grain sample (step 1104). Method 1100 also includes running the purified DNA sample in a qPCR reaction, the qPCR reaction comprising at least two different fluorescent probes (e.g., FAM and VIC labeled nucleic acid probes) that competitively bind to the same DNA locus in which the DNA locus is indicative of the presence or absence of a transgenic trait (step 1106). In some embodiments, the transgenic trait is glyphosate resistance, and method 1100 identifies the genetic sequence that confers glyphosate resistance. Method 1100 further includes generating results of the qPCR reaction that characterize the competitive binding levels of each of the at least two different fluorescent probes during each cycle of the qPCR reaction (step 1108). In some embodiments, for example, the results of the qPCR reaction input into the support vector machine model comprise the ratio of the fluorescence values of FAM/(FAM+VIC). In addition, method 1100 also includes interpreting the results with one or more of a machine learning model (e.g., a support vector machine model or the like), ratiometric regression algorithm, or best fit model to determine the fractional abundance of the transgenic trait (step 1110). Typically, the time elapsed from processing the grain sample to detecting the fractional abundance of the transgenic trait is 15 minutes or less.

In some embodiments of method 1100, the results of the qPCR reaction that characterize the competitive binding levels of each of the at least two different fluorescent probes during each cycle of the qPCR reaction are at least one of a standard curve or an N-dimensional curve. In some embodiments of method 1100, a machine learning model is used, and the machine learning model has been trained on a range of grain samples comprising levels from 0-100% of transgenic grain in increments of 30% or less (e.g., in 10% increments, in 5% increments, or less).

Labeling

The oligonucleotides (e.g., primers, probes, etc.) described herein are optionally labeled, e.g., to facilitate subsequent detection. In some embodiments, the nucleic acid synthesis reagents (e.g., phosphoramidite precursors of nucleotides, etc.) are labeled prior to synthesis of the primer or probe nucleic acids. In certain embodiments, labels and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, phosphorous-nitrogen bonds, etc.). Optionally, a linker attaches the label to a given nucleotide. A wide variety of linkers can be used or adapted for use in conjugating labels and nucleotides. Certain non-limiting illustrations of such linkers are referred to herein.

Essentially any label is optionally utilized to label the nucleotides and nucleosides utilized in the oligonuclotides (e.g., primers, probes, etc.) described herein. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIG-DYE® v 1 dyes, BIGDYE® v 2 dyes, BIGDYE® v 3 dyes, etc.), *Lucifer* dyes (e.g., *Lucifer* yellow, etc.), CASCADE BLUE®, Oregon Green, and the like. Other labels optionally adapted for use in the methods disclosed herein include, e.g., biotin, weakly fluorescent labels (Yin et al. (2003) Appl Environ Microbiol. 69(7):3938, Babendure et al. (2003) Anal. Biochem. 317(1): 1, and Jankowiak et al. (2003) Chem Res Toxicol. 16(3):304), non-fluorescent labels, calorimetric labels, chemiluminescent labels (Wilson et al. (2003) Analyst. 128(5):480 and Roda et al. (2003) Luminescence 18(2):72), Raman labels, electrochemical labels, radioisotope labels, and bioluminescent labels (Kitayama et al. (2003) Photochem Photobiol. 77(3):333, Arakawa et al. (2003) Anal. Biochem. 314(2):206, and Maeda (2003) J. Pharm. Biomed. Anal. 30(6): 1725), among many others.

A large variety of linkers are available for linking labels to nucleic acids and will be apparent to one of skill in the art. A linker is generally of a structure that is sterically and electronically suitable for incorporation into a nucleic acid. Linkers optionally include, e.g., ether, thioether, carboxamide, sulfonamide, urea, urethane, hydrazine, or other moieties. To further illustrate, linkers generally include between about one and about 25 nonhydrogen atoms selected from, e.g., C, N, O, P, Si, S, etc., and comprise essentially any combination of, e.g., ether, thioether, amine, ester, carboxamide, sulfonamide, hydrazide bonds and aromatic or heteroaromatic bonds. In some embodiments, for example, a linker comprises a combination of single carbon-carbon bonds and carboxamide or thioether bonds. Although longer linear segments of linkers are optionally utilized, the longest linear segment typically contains between about three to about 15 nonhydrogen atoms, including one or more heteroatoms.

Reaction Mixtures

The methods disclosed herein optionally utilize various reaction mixtures that can be used in a wide variety of applications, particularly where it is desirable to determine the fractional abundance of target nucleic acids in amplification reactions. In some embodiments, for example, reaction mixtures are utilized in performing homogeneous amplification/detection assays (e.g., real-time PCR monitoring), or detecting mutations or genotyping nucleic acids. In certain embodiments, multiple primers and/or probes are pooled together in reaction mixtures for use in applications that involve multiplex formats. Many of these applications are described further herein.

In addition to the oligonucleotides (e.g., primers and probes), reaction mixtures also generally include various reagents that are useful in performing, e.g., nucleotide polymerization, nucleic acid amplification and detection reactions (e.g., real-time PCR monitoring or 5'-nuclease assays), and the like. Exemplary types of these other reagents include, e.g., template or target nucleic acids (e.g., obtained or derived from essentially any source), reference nucleic acids, nucleotides, pyrophosphate, light emission modifiers, biocatalysts (e.g., DNA polymerases, RNA polymerases, etc.), buffers, salts, amplicons, glycerol, metal ions (e.g., $Mg^{+2}$, etc.), dimethyl sulfoxide (DMSO), poly rA (e.g., as a carrier nucleic acid for low copy number targets), uracil N-glycosylase (UNG) (e.g., to protect against carry-over contamination). In some kinetic PCR-related applications, reaction mixtures also include probes that facilitate the detection of amplification products. Examples of probes used in these processes include, e.g., hybridization probes, exonuclease probes (e.g., 5'-nuclease probes), and/or hairpin probes.

Exemplary Systems and Computer Readable Media

Figure 6:
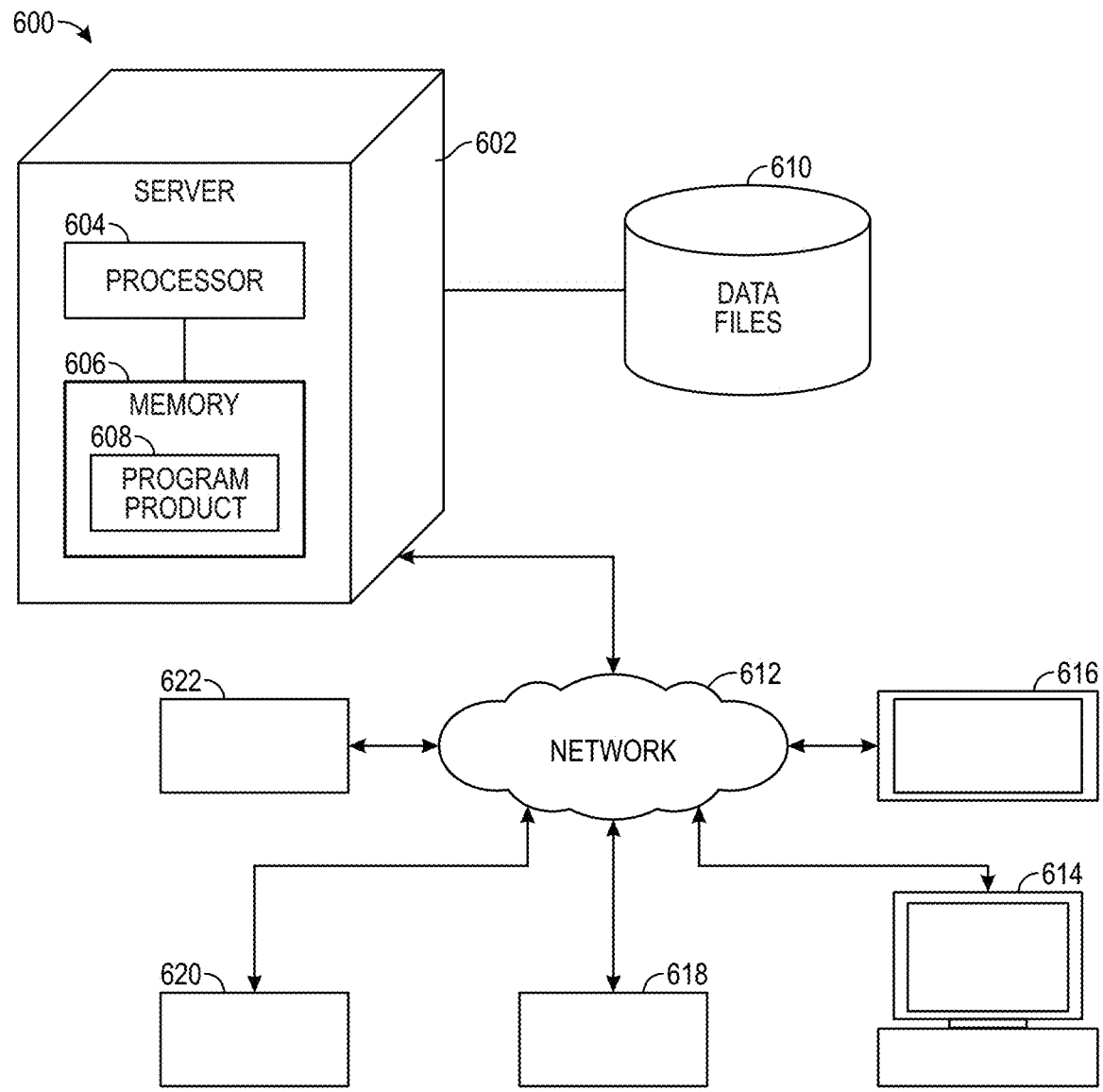
FIG. 6 is a schematic diagram of an exemplary system suitable for use with certain embodiments.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 6 provides a schematic diagram of an exemplary system suitable for use with implementing at least aspects of the methods disclosed in this application. As shown, system 600 includes at least one controller or computer, e.g., server 602 (e.g., a search engine server), which includes processor 604 and memory, storage device, or memory component 606, and one or more other communication devices 614, 616, (e.g., client-side computer terminals, telephones, tablets, laptops, other mobile devices, etc. (e.g., for receiving captured images for further analysis, etc.)) positioned remote from nucleic acid amplification component (e.g., a thermocycler or the like) 618, sample preparation component 620, and material transfer component 622, and in communication with the remote server 602, through electronic communication network 612, such as the Internet or other internetwork. Communication devices 614, 616 typically include an electronic display (e.g., an internet enabled computer or the like) in communication with, e.g., server 602 computer over network 612 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 600 also includes program product 608 stored on a computer or machine readable medium, such as, for example, one or more of various types of memory, such as memory 606 of server 602, that is readable by the server 602, to facilitate, for example, a guided search application or other executable by one or more other communication devices, such as 614 (schematically shown as a desktop or personal computer). In some aspects, system 600 optionally also includes at least one database server, such as, for example, server 610 associated with an online website having data stored thereon (e.g., entries corresponding to more reference images, indexed therapies, etc.) searchable either directly or through search engine server 602. System 600 optionally also includes one or more other servers positioned remotely from server 602, each of which are optionally associated with one or more database servers 610 located remotely or located local to each of the other servers. The other servers can beneficially provide service to geographically remote users and enhance geographically distributed operations.

As understood by those of ordinary skill in the art, memory 606 of the server 602 optionally includes volatile and/or nonvolatile memory including, for example, RAM, ROM, and magnetic or optical disks, among others. It is also understood by those of ordinary skill in the art that although illustrated as a single server, the illustrated configuration of server 602 is given only by way of example and that other types of servers or computers configured according to various other methodologies or architectures can also be used. Server 602 shown schematically in FIG. 6, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 600. As also understood by those of ordinary skill in the art, other user communication devices 614, 616 in these aspects, for example, can be a laptop, desktop, tablet, personal digital assistant (PDA), cell phone, server, or other types of computers. As known and understood by those of ordinary skill in the art, network 612 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 608 is optionally in the form of microcode, programs, cloud computing format, routines, and/or symbolic languages that provide one or more sets of ordered operations that control the functioning of the hardware and direct its operation. Program product 608, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 608 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 608 is optionally copied from the computer-readable medium to a hard disk or a similar intermediate storage medium. When program product 608, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes at least one captured tissue images and/or the like to be displayed (e.g., via communication devices 614, 616 or the like) and/or receive information from other system components and/or from a system user (e.g., via communication devices 614, 616, or the like).

In some aspects, program product 608 includes non-transitory computer-executable instructions which, when executed by electronic processor 604 perform at least: determining a ratio of detectable signal levels detected for at least a first target nucleic acid to detectable signal levels detected for at least a first reference nucleic acid to produce at least a first set of relative detectable signal level ratios from amplification data that comprises one or more detectable signal levels detected as the first target nucleic acid and the first reference nucleic acid are amplified in a reaction mixture; determining a ratio of the detectable signal levels detected for the first target nucleic acid to a cumulative total of the detectable signal levels detected for the first target nucleic acid and for the first reference nucleic acid to produce at least a first set of cumulative detectable signal level ratios; and determining a fractional abundance of at least a first target variant in a population at and/or after the quantitation threshold (Cq) value for the first target nucleic acid from the first set of relative detectable signal level ratios and/or the first set of cumulative detectable signal level ratios and at least one N-dimensional standard curve generated from calibration data of known fractional abundance, where N is a number of ratios at different cycle numbers, to determine the fractional abundance of the target variant in the population. In some embodiments, program product 608 includes non-transitory computer-executable instructions which, when executed by electronic processor 604 perform at least: receive results of qPCR reactions that characterize the competitive binding levels of each of at least two different fluorescent probes during each cycle of a qPCR reaction, and interpret the results with one or more of a machine learning model, ratiometric regression algorithm, or best fit model to determine the fractional abundance of a given transgenic trait in a sample.

System 600 also typically includes additional system components (e.g., nucleic acid amplification component (e.g., a thermocycler or the like) 618, sample preparation component 620, and material transfer component 622) that are configured to perform various aspects of the methods described herein. In some of these aspects, one or more of these additional system components are positioned remote from and in communication with the remote server 602 through electronic communication network 612, whereas in other aspects, one or more of these additional system components are positioned local, and in communication with server 602 (i.e., in the absence of electronic communication network 612) or directly with, for example, desktop computer 614.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7th Ed. (2016), Elmasri, *Fundamentals of Database Systems*, Addison Wesley, 6th Ed. (2010), Coronel, *Database Systems: Design, Implementation, & Management*, Cengage Learning, 11th Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), which are each incorporated by reference in their entirety.

Example 1

Methods
a. Generation of Calibration qPCR Data

A duplex PCR assay was designed for multiplexed detection of two allelic targets from two distinct maize strains, referred to as Gene A and Gene B from hereon, with PCR primers and exonuclease probes labeled with FAM and VIC fluorophores respectively. Mixtures of purified genomic DNA from maize strains containing either Gene A or Gene B were mixed to create calibration samples containing FAs of 0% to 100% of Gene B in 5% increments. In a 384 well PCR plate, these samples were spiked into 9 replicates of 5 µL volume PCR reactions for each FA with a total combined DNA input of 48 ng per reaction. This was repeated with the same conditions except 6 replicates at each FA for the same DNA concentration, and 6 replicates wherein the DNA input was decreased to 4.8 ng per reaction to assess effect of varying sample content. All reactions in 384-well plates were subjected to 40 cycles of 3-step qPCR on a benchtop thermocycler (Applied Biosystems QuantStudio 7 Flex Real-Time PCR system) with fluorescence measurements acquired at the end of the extension step. Analysis of quantitation cycle (Cq) for each FAM and VIC curve was exported from the built-in QuantStudio software. Raw fluorescence data was baseline subtracted for each reaction by subtracting the minimum fluorescence value of each respective well.

b. Fluorescence Ratio Calculation

Cycles assigned to fluorescence data were adjusted for each well by subtracting the nearest integer value to the VIC Cq from all cycle numbers. The resulting adjusted cycle numbers greater than or equal to zero corresponded to fluorescence data with visible qPCR amplification signals, and thus could produce meaningful ratiometric data. Fluorescence ratios were calculated for each cycle with the following equation (1):

$$F_{ratio} = \frac{F_{FAM}}{F_{FAM} + F_{VIC}} \quad (1)$$

where $F_{VIC}$ is the baseline subtracted fluorescence for the VIC curve at a given cycle number, $F_{FAM}$ is the baseline subtracted fluorescence for the FAM curve at the same cycle number, and $F_{ratio}$ is the resulting fluorescence ratio.

c. Univariate Logistic Regression

For each adjusted cycle value from 0 to 10 cycles after VIC Cq, the FA values were fit to the fluorescence ratios for the given cycle using the following equation (2):

$$FA = \frac{a}{1 + b*c^{-(R(x)-d)}} + e \quad (2)$$

where FA is the predicted FA, R is the fluorescence ratio at a given cycle, x, and a, b, C, d, and, e are constants. Fits were calculated using an R implementation of the Levenberg-Marquardt nonlinear least squares algorithm.

d. Bivariate Weighted Regression

To increase the dimensionality of fits to include data from multiple cycles after VIC Cq, all possible pairs of the univariate logistic regressions were fit to the calibration data fluorescence ratios with parabolic weighting. Regression of the fits to calculate weighting values was achieved with the same R Levenberg-Marquardt algorithm for the following form (3):

$$FA_{x,y} = w_{x1}*(ratio_x - w_{x2})^2 FA_x + w_{y1}*(ratio_y - w_{y2})^2 FA_y \quad (3)$$

where $FA_{x,y}$ is the output predicted FA, all w values are constant weights, $ratio_x$ and $ratio_y$ are the fluorescence ratios at cycle x and y respectively, and $FA_x$ and $FA_y$ are the logistic fits corresponding to equation (2) for cycle x and y.

e. Fitting Accuracy and Resolution Assessment

The best fits for modeling FA were determined by calculating the residual sum of squares (RSS) for both univariate and bivariate fits and selecting the model with the lowest RSS value. Once the most accurate model was selected, its performance was assessed with a simulation completed in R. The raw fluorescence data from the qPCR calibration reactions for each FA value was pooled as a mock population of reactions with 21 replicates per FA increment. For each FA value from 0 to 100%, one of the replicates was randomly selected and the error between the predicted FA from the model and the known FA was recorded. This random selection was repeated 100 times with replacement to generate an average and standard deviation of the prediction error. Higher sampling sizes (3 replicates and 5 replicates) were simulated using the same setup except multiple samples were selected with replacement for each round and the predicted FA was calculated from the average of individual FA values generated for each selection using the model.

Results and Discussion

Figure 7A:
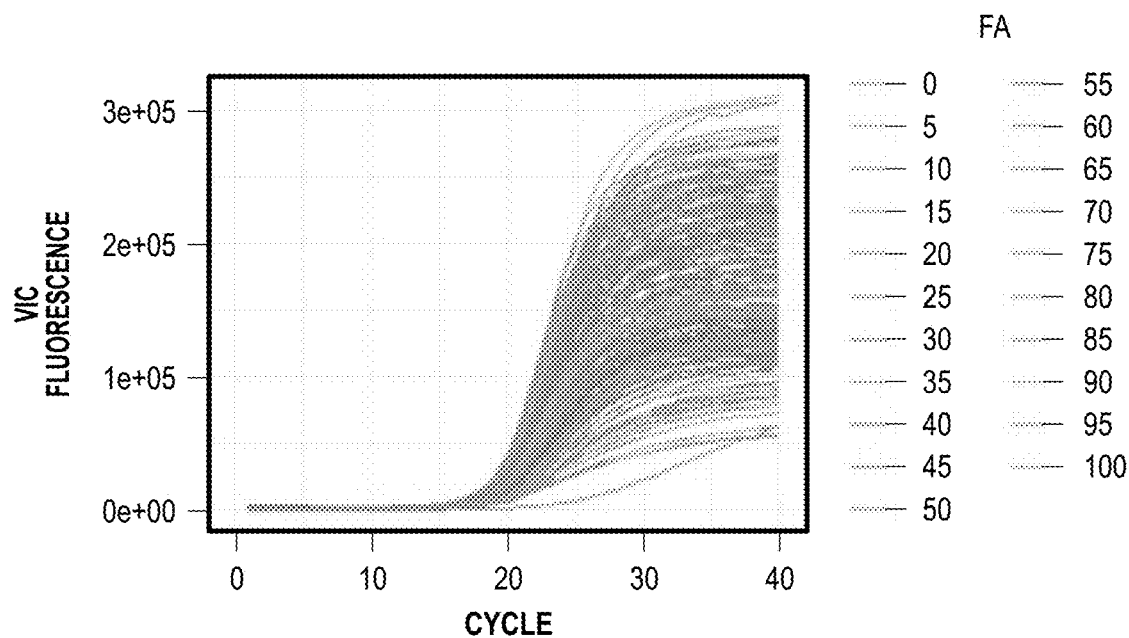
FIG. 7A shows a plot of baseline-subtracted qPCR data of VIC fluorescence for all qPCR runs resulting from steps 1-2 in the standard curve algorithm (FIG. 5) in which VIC fluorescence is represented on the y-axis and the cycle number is represented on the x-axis.
Figure 7B:
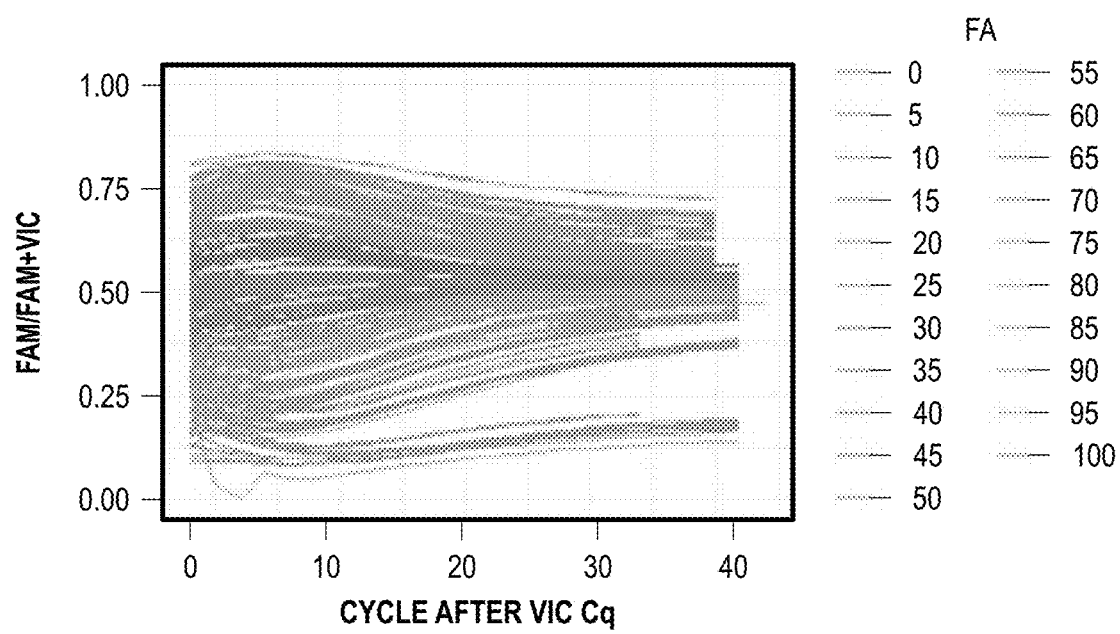
FIG. 7B shows a plot of ratiometric curves generated from FAM and VIC qPCR data with steps 3-4 in the standard curve algorithm (FIG. 5) in which fluorescence ratios (FAM/FAM+VIC) are represented on the y-axis and the cycle number is represented on the x-axis.
Figure 8A:
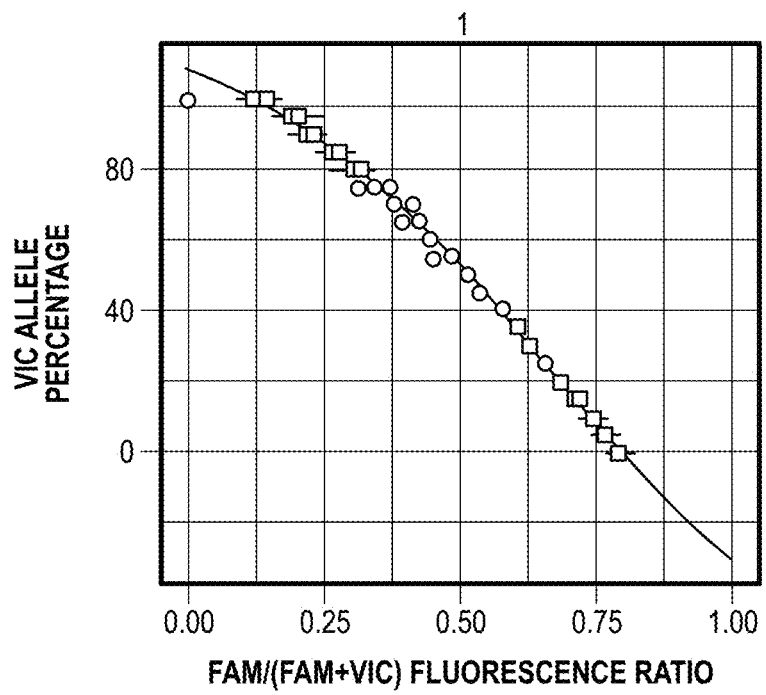
FIGS. 8A-J are logistic regression plots at each cycle after VIC Cq. In particular, fractional abundance of the VIC allele (y-axis) is plotted as a function of the fluorescence ratios (x-axis) at each cycle after the VIC Cq (listed directly above each plot). The ratios at each fractional abundance/allele percentage across all replicates is represented by horizontal boxplots with the corresponding logistic regression curve overlaid as a solid black line.
Figure 8B:
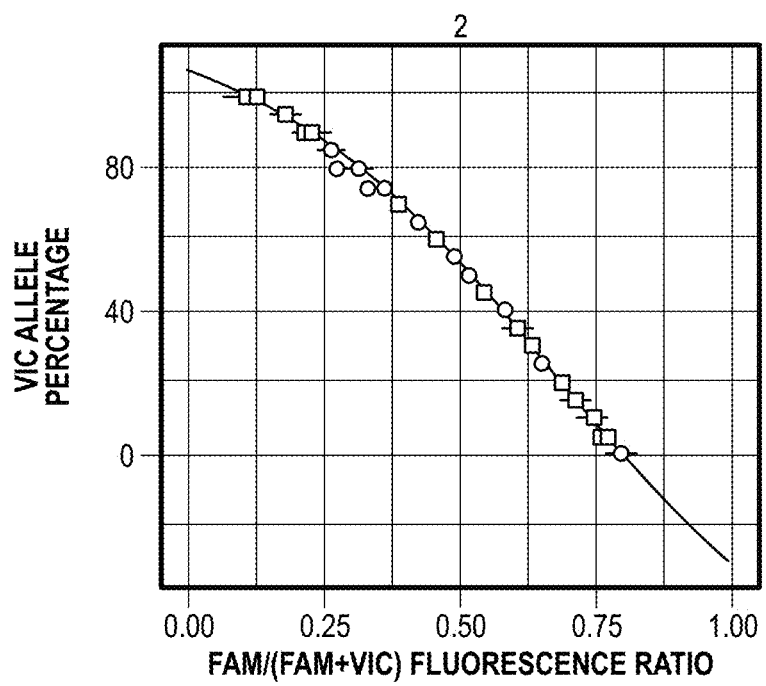
Figure 8C:
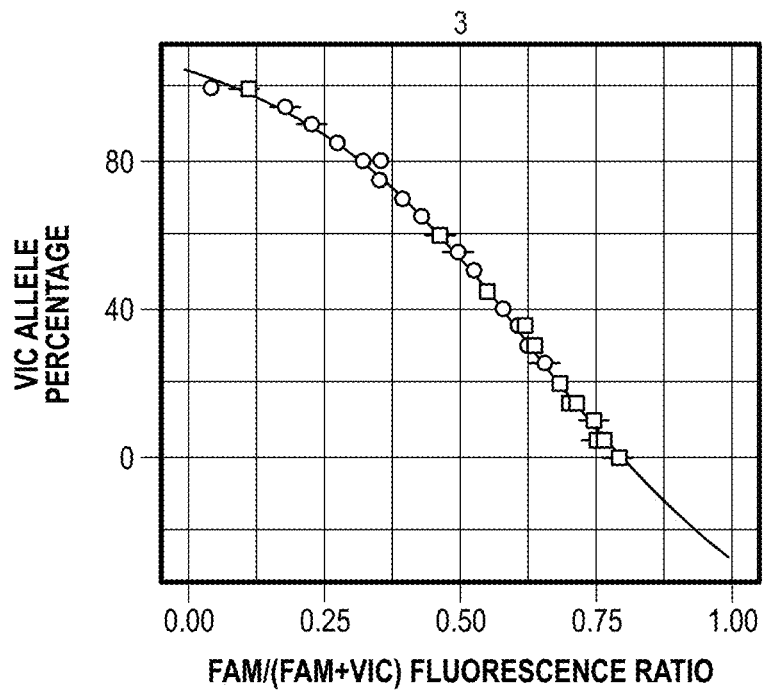
Figure 8D:
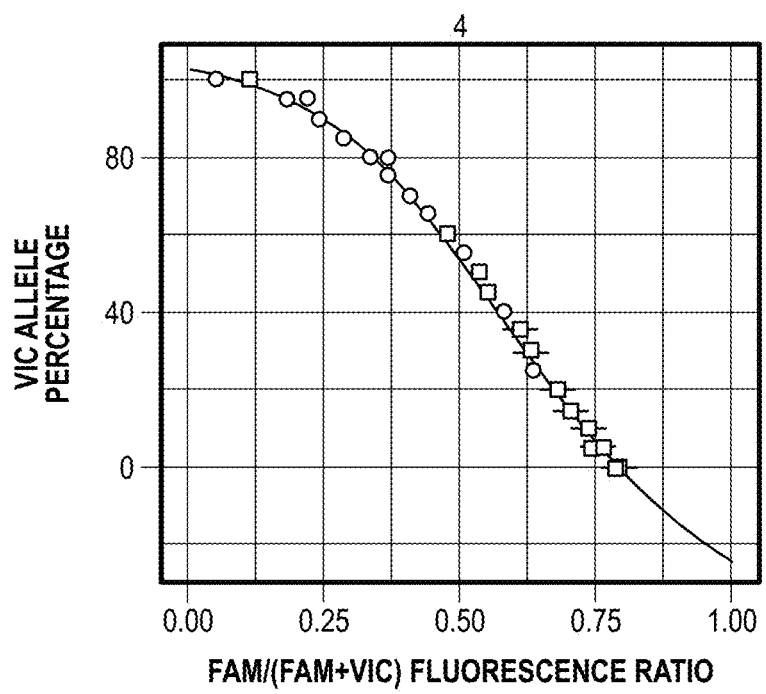
Figure 8E:
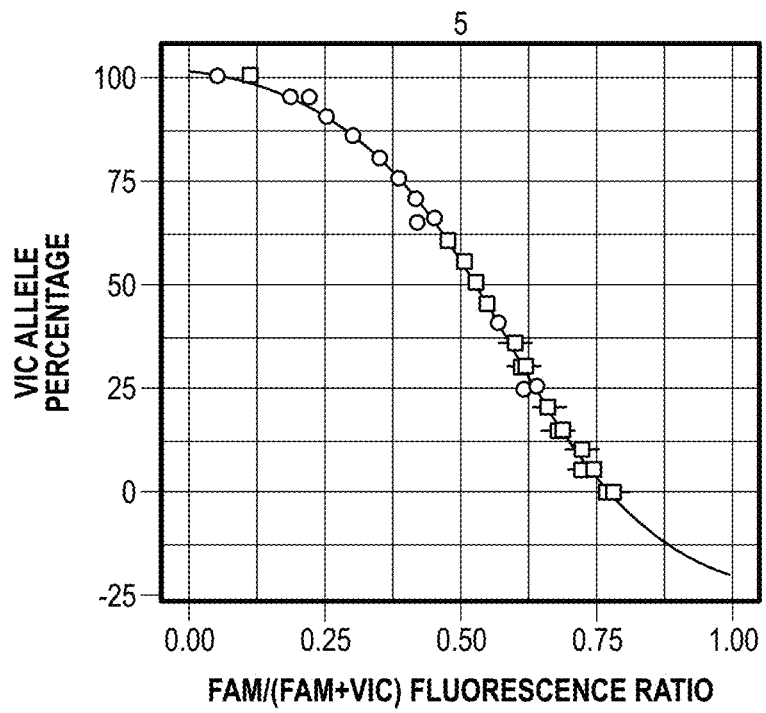
Figure 8F:
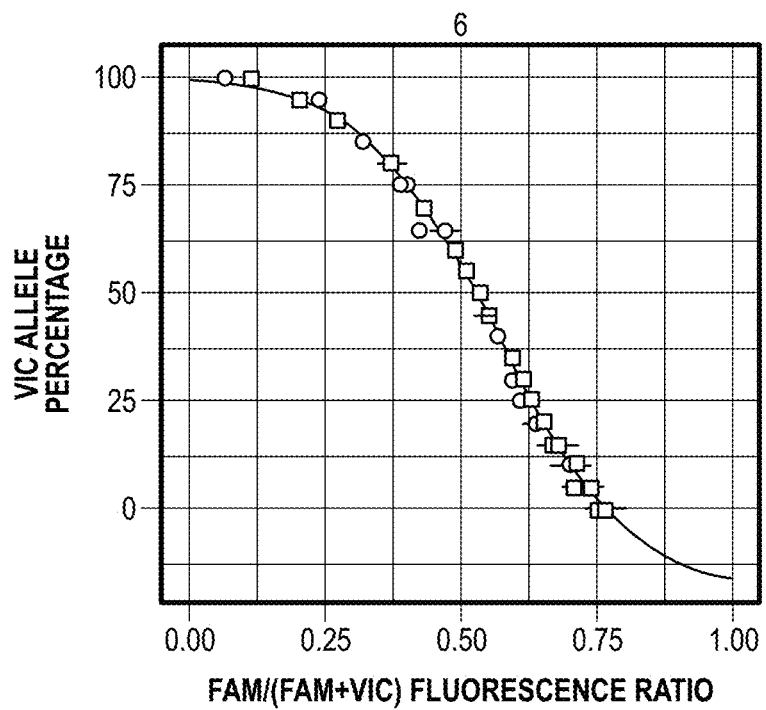
Figure 8G:
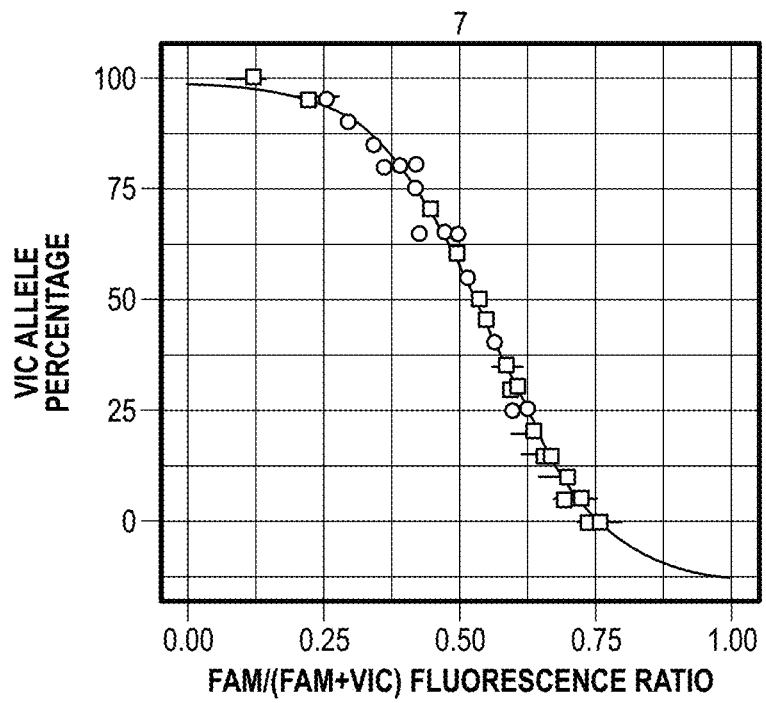
Figure 8H:
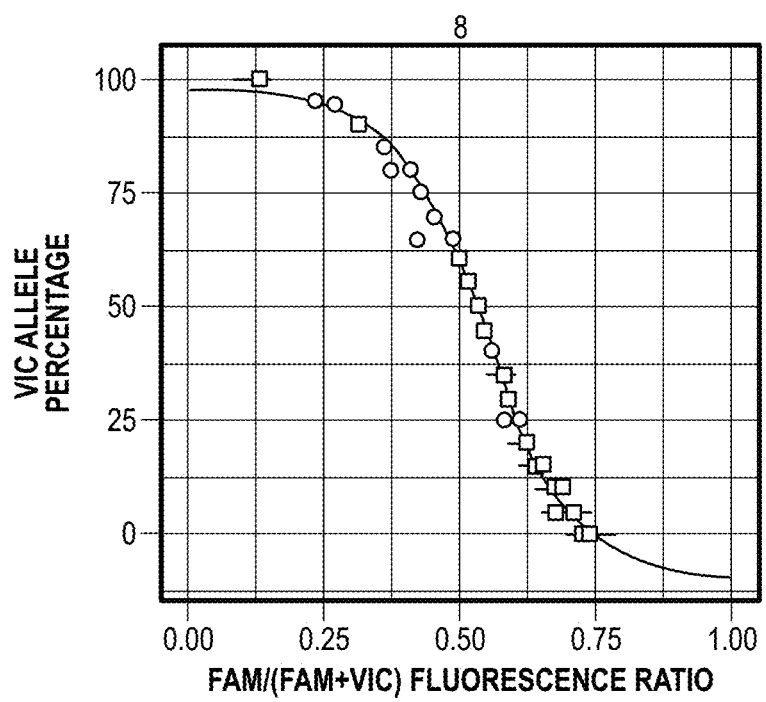
Figure 8I:
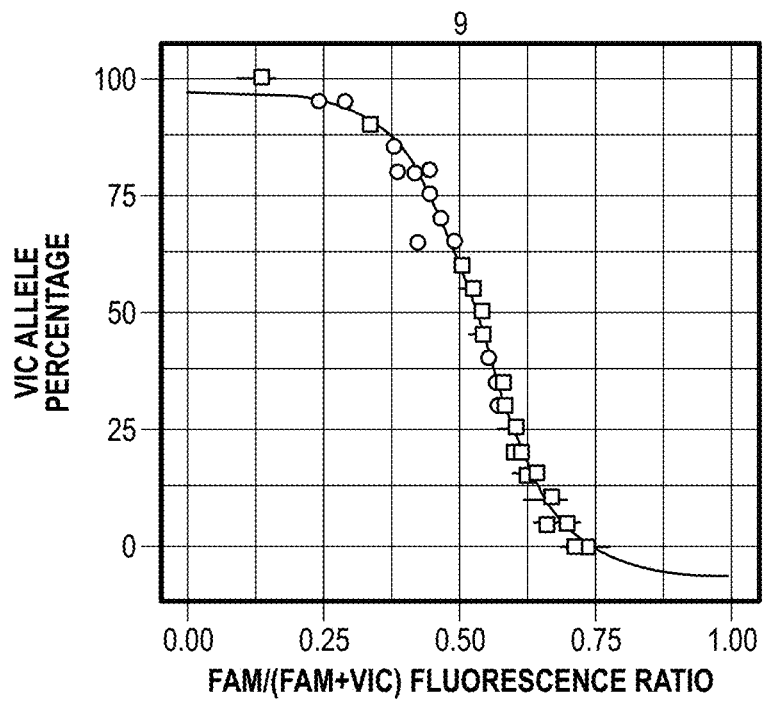
Figure 8J:
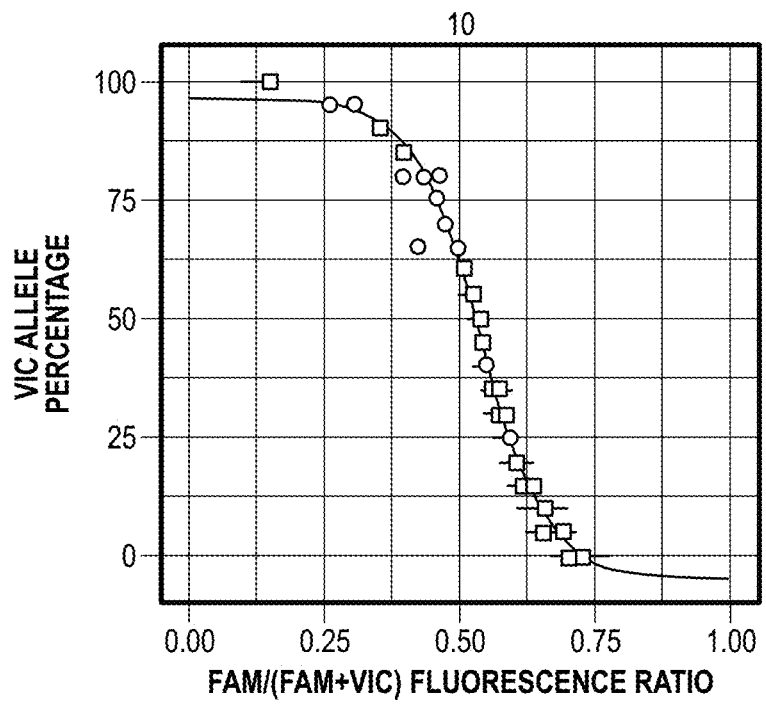

Baseline subtraction of qPCR data yielded curves with highly significant overlap which rendered quantification by Cq values with discrimination in 5% VIC FA increments unattainable (FIG. 7A). After cycle adjustment and fluorescence ratio extraction (FIG. 5—steps 4 and 5), the resulting ratiometric curves are visually distinguishable for each FA value with minimal overlap (FIG. 7B). As the cycle after VIC Cq value increases, the majority of ratiometric curves draw nearer to convergence at 0.5 as the fluorescence saturates for both probes. Separation between ratiometric curves in adjacent 5% FA increments are evident between cycle 1 and cycle 8 after VIC Cq. To encompass this region, univariate logistic regression fits were calculated for data at cycle 0 through cycle 10 after VIC Cq (FIGS. 8A-J).

Univariate fits at lower cycle numbers are more linear in the ratio range from 0 to 1, while increasing cycle number produces more traditional logistic shapes as a result of saturation of one or both probe signals. The more linear curves have greater resolution for central values of VIC FA (changes in ratios near 0.5 result in relatively smaller changes in the predicted FA), and the asymptotic curves of the later cycles better resolve small differences in FA at the extremes of the ratio values closer to 0 or 1. Because of this logistic fit conformation change, a parabolic weighting scheme was implemented to allow for stronger weighting of the low cycle fits when inputting central fluorescence ratios and stronger weighting of high cycle fits for the ratios at the extremes.

Bivariate fits with parabolic weighting that included cycles after VIC Cq under 7 unilaterally produced better fits than the univariate fits as determined by RSS (Table 1, Table 2). The best univariate fit (i.e. lowest RSS) was cycle 5 while the best overall fit combined univariate fits of cycle 2 and 5 with the following equation from previously defined equations (2) and (3):

$$FA_{2.5} = w_{2a} * (\text{ratio}_2 - w_{2b})^2 FA_2 + w_{5a} * (\text{ratio}_5 - w_{5b})^2 FA_5 \quad (4.1)$$

$$w_{2a} = 51.58319, w_{2b} = -0.07991123$$

$$w_{5a} = -0.2616249, w_{5b} = 9.117226$$

$$FA_2 = \frac{206.0570}{1 + 1.006860 * (2.976069e - 02)^{-(\text{ratio}_2 - 0.6843884)}} - 81.631120 \quad (4.2)$$

$$FA_5 = \frac{131.7516}{1 + 1.279303 * (1.290031e - 03)^{-(\text{ratio}_2 - 0.6183107)}} - 27.628891 \quad (4.3)$$

Figure 9C:
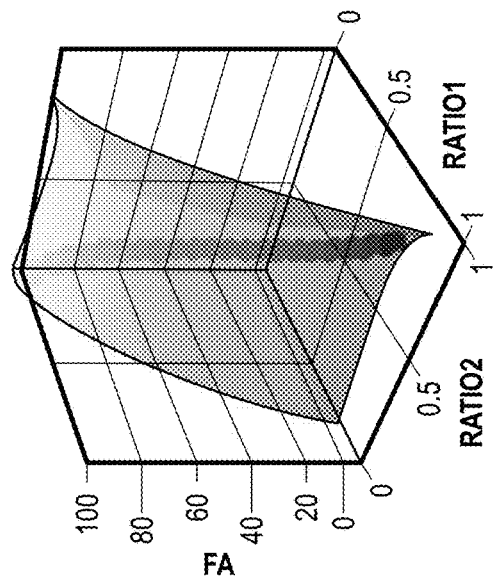
FIGS. 9A-C show a plot of a best bivariate fit (cycle 2 and cycle 5) curve. The curve represented by the multidimensional regression fit illustrates the predicted fractional abundance (FA) values given inputs of fluorescence ratios at 2 cycles after VIC Cq (Ratio1) and 5 cycles after VIC Cq (Ratio2).
Figure 9B:
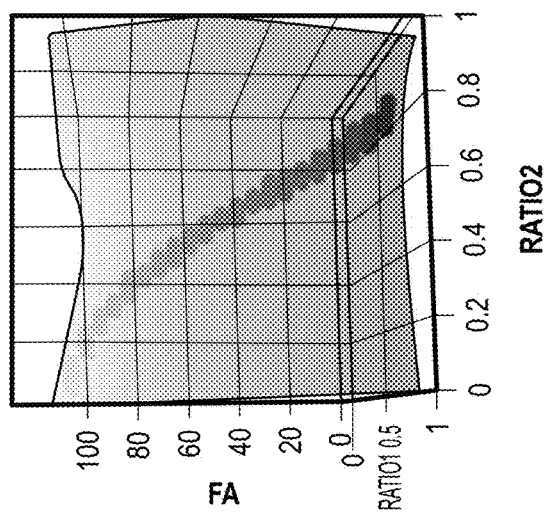
Figure 9A:
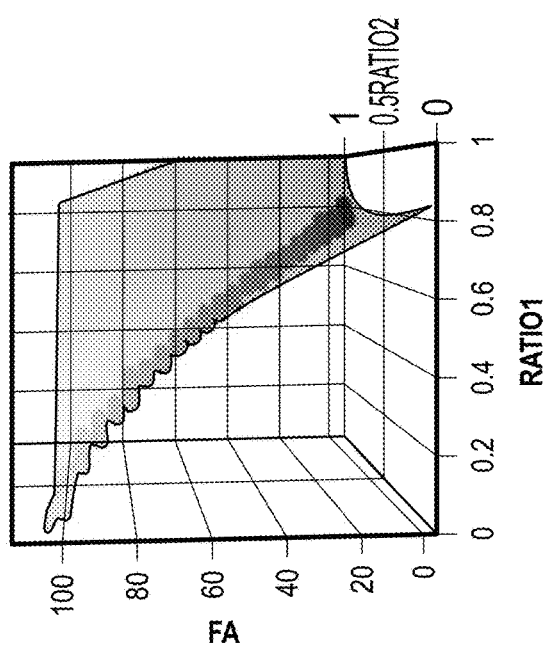

The curve defined by equations 4.1-4.3 is shown in FIG. 9 with corresponding individual reaction data points overlaid and all greyscale coded by FA value.

TABLE 1

Residual Sum Squared (RSS) of Univariate Fits

| Cycle | RSS |
| --- | --- |
| 0 | 421178 |
| 1 | 413616 |
| 2 | 413777 |
| 3 | 419293 |
| 4 | 432708 |
| 5 | 44870 |
| 6 | 59631 |
| 7 | 94362 |
| 8 | 269552 |
| 9 | 364565 |
| 10 | 553199 |

TABLE 2

Residual Sum Squared (RSS) of Bivariate Fits

| | | Cycle-2 | | | | | | | | | |
| --- | --- | --- | --- | --- | --- | --- | --- | --- | --- | --- | --- |
| | | 0 | 1 | 2 | 3 | 4 | 5 | 6 | 7 | 8 | 9 |
| Cycle-1 | 1 | 3106 | | | | | | | | | |
| | 2 | 2500 | 3065 | | | | | | | | |
| | 3 | 6920 | 2964 | 2967 | | | | | | | |
| | 4 | 25296 | 2357 | 2147 | 2593 | | | | | | |
| | 5 | 3169 | 2128 | 1845 | 2058 | 3228 | | | | | |
| | 6 | 8417 | 7094 | 4784 | 4709 | 5200 | 5532 | | | | |
| | 7 | 25750 | 20605 | 17307 | 14459 | 12484 | 11121 | 12375 | | | |
| | 8 | 127824 | 126313 | 14004 | 13690 | 14146 | 14701 | 148886 | 203812 | | |
| | 9 | 152283 | 150213 | 150324 | 13934 | 17393 | 44283 | 20505 | 17807 | 261468 | |
| | 10 | 188215 | 185370 | 24589 | 29098 | 35245 | 44304 | 58861 | 93365 | 268085 | 360815 |

Figure 10A:
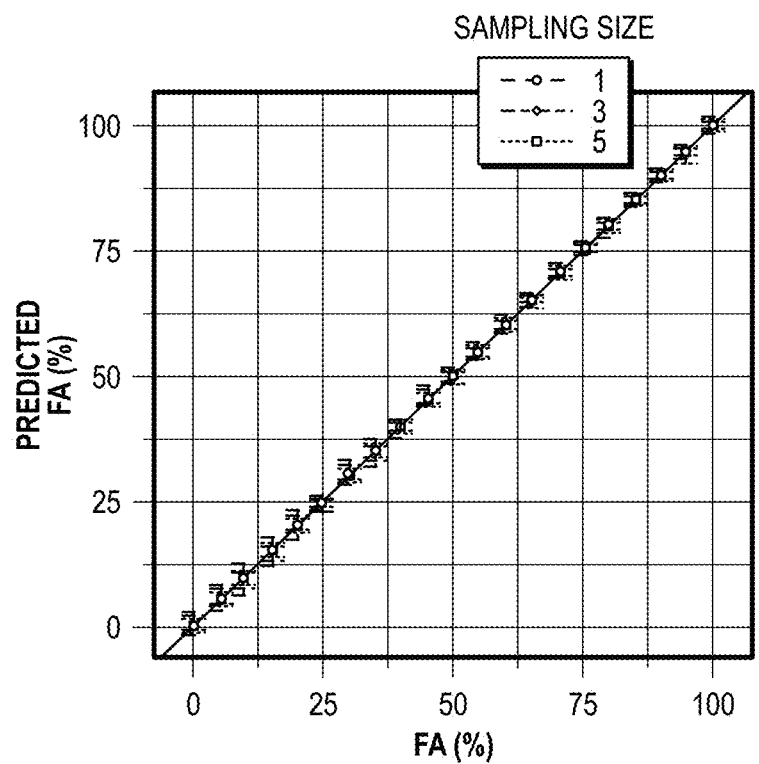
FIG. 10A is a plot (predicted FA (%) is represented on the y-axis, FA (%) is represented on the x-axis) showing the resulting averages of FA predictions with error bars denoting standard deviation for each sampling size.
Figure 10B:
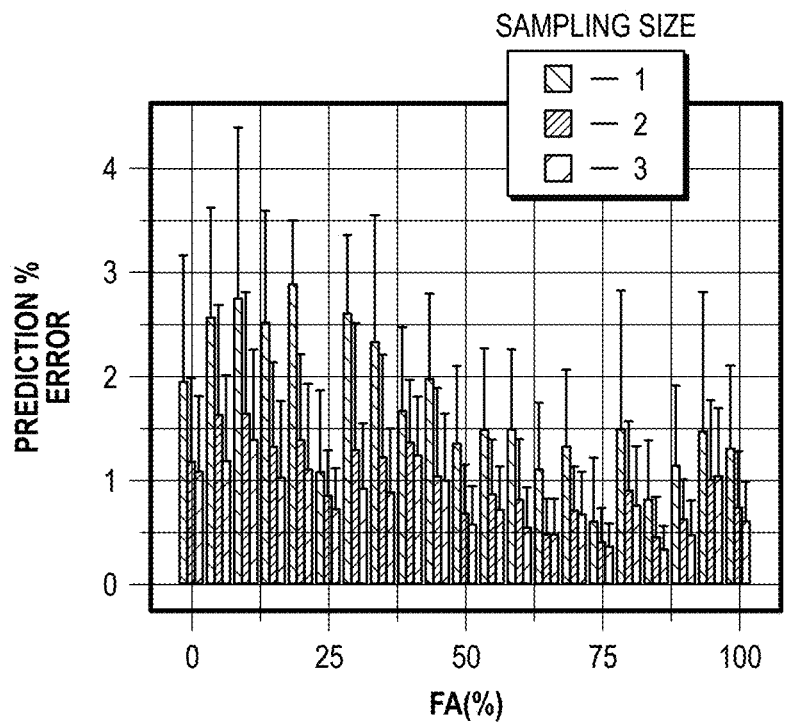
FIG. 10B is a bar plot (prediction % error is represented on the y-axis, FA (%) is represented on the x-axis) representing the average absolute error in the predicted FA for each true FA value and sampling size. Error bars denote standard deviation of the error for the 100 trials.

Simulation results demonstrate that with a selection of a single reaction, the average absolute error in prediction across all FA values remains <3% (FIGS. 10 A and B). Increasing sample size for FA prediction to 3 and 5 replicates further decreases average error across the full range of FA increments to <2% and <1.5% respectively. These results demonstrate conclusively the potential for qRR-PCR analysis to allow quantification with a resolution <5%.

The ability to quantify with high resolution standard bulk PCR has great advantages over digital PCR techniques in terms of possible dynamic range, simplicity of assay disposables and instrumentation, and ease of adoption with already existing assays that have not been optimized for single copy sensitivity. Even higher resolution beyond that demonstrated is also possible with higher dimensionality in the final fitting models to leverage more of the ratiometric data that is left unused or alternative weighting schemes. This technique can be expanded to include higher multiplexing within each reaction to evaluate FA of more than one gene or other target nucleic acid against a reference gene.

CONCLUSIONS

The exemplary algorithm described in this example has been developed for analysis of multiplexed qPCR reactions to enable quantitation with resolution <5%. This algorithm produces estimates of FA with regression of ratiometric relationships between the simultaneous amplification of a target and control gene or other nucleic acid. Analysis by this exemplary method is compatible with data generated from all standard real-time PCR thermocyclers without necessitating the complex fluidics or expensive fabricated devices that are used in digital PCR for absolute genetic quantification. The ability to quantify genetic expression with high fidelity and resolution has broad ranging applications across disciplines in healthcare, livestock, and agricultural settings, among many other applications.

Example 2

Problem: Until now, cost effective methods of detecting transgenic grain present in a grain sample have been limited to a present/absent type of detection. However, there is a growing need in agriculture for a rapid and inexpensive method of detecting the relative amount of the grain with the transgenic traits present in the grain sample as versus the grain without the transgenic trait or with a different transgenic trait present in the grain sample.

Solution: Using standard qPCR techniques, relative values of at least two fluorescent labels may be simultaneously detected. This example shows that with proper optimization and design of target specific probes, it is possible to use these relative fluorescent values to rapidly determine the relative amount of a specific transgenic trait with up to a 5% degree of accuracy.

While this can be accomplished with a ratiometric regression algorithm, a fitting technique, or an N-dimensional curve, utilizing a Support Vector Machine (SVM) based determination has been shown to provide an excellent balance of speed and precision.

Three datasets with different markers were used to identify algorithms that can predict fractional abundance, one collected on the ENLIST marker, two collected on the Conkesta marker.

In each dataset, captured raw PCR data of FAM and VIC values was used. These fluorescence values utilized the complementary relationship of the gene of interest and the values were transformed into a FV ratio.

Figure 12A:
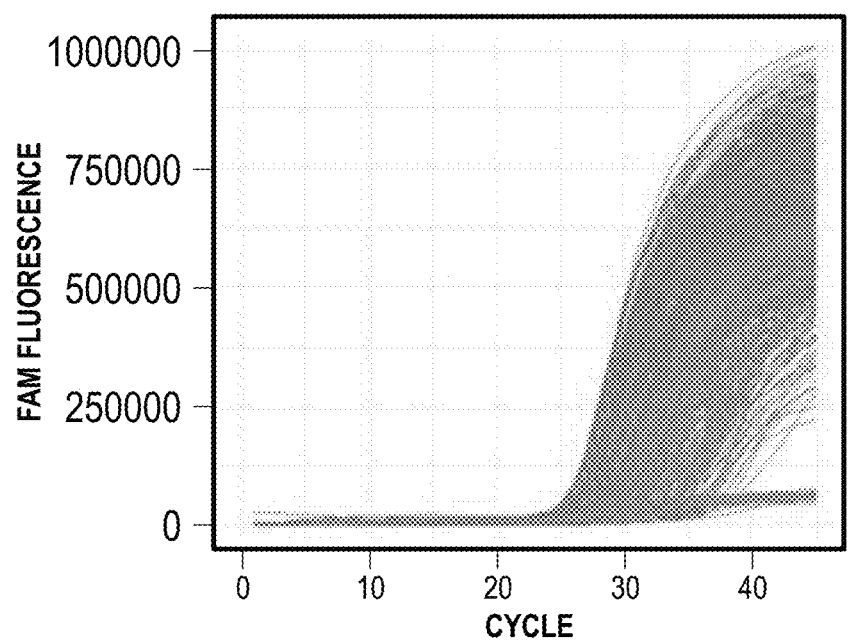
FIGS. 12 A and B are plots showing raw PCR data (FAM Fluorescence is represented on the y-axis and Cycle Number is represented on the x-axis (FIG. 12A), and VIC Fluorescence is represented on the y-axis and Cycle Number is represented on the x-axis (FIG. 12B)).
Figure 12B:
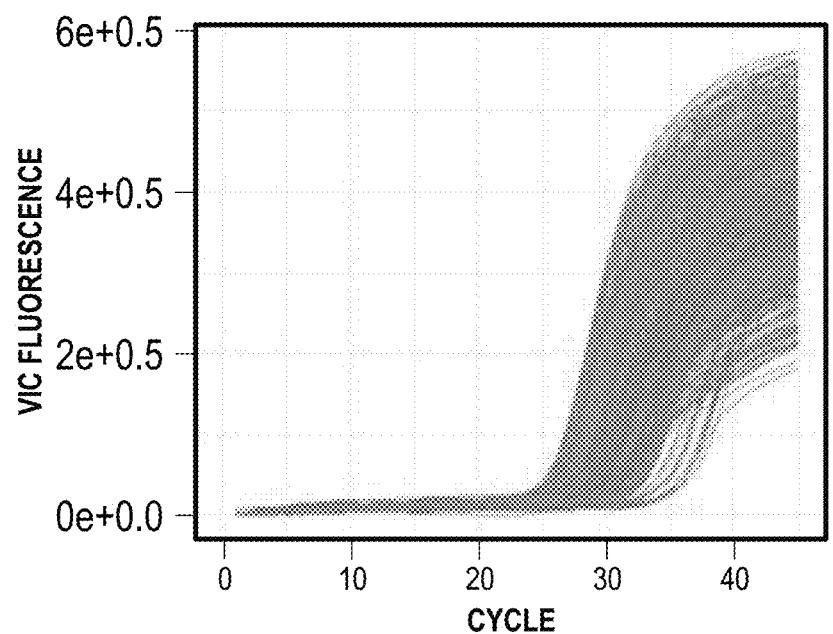
Figure 13:
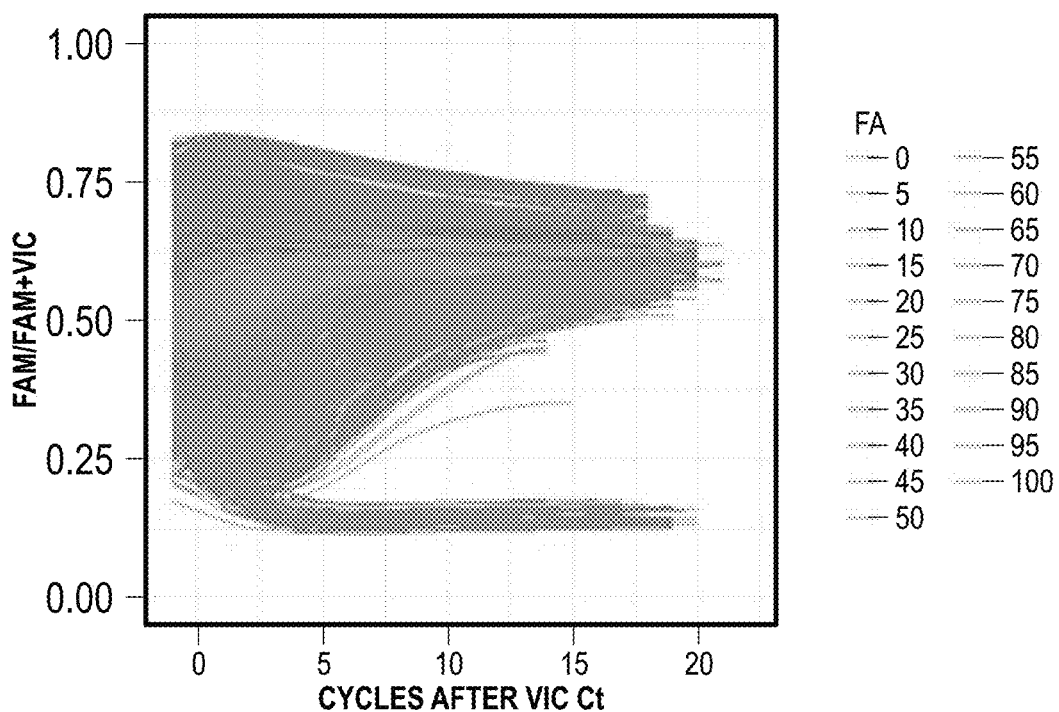
FIG. 13 is a plot showing typical curves of fluorescence ratios with adjusted Cycle time and by VIC Ct (FAM/FAM+VIC Fluorescence is represented on the y-axis and Cycle Number After VIC Ct is represented on the x-axis).

FIGS. 12 A and B show typical raw fluorescence values of FAM and VIC, respectively. FIG. 13 shows the fluorescence ratios with cycle adjusted by VIC cycle threshold, which is the number of cycles required for the fluorescent signal to exceed background level.

The SVM algorithm was used to focus on the separation between fractional abundance curves. The SVM model learned from the florescence curves in the training dataset to predict percent of fractional abundance. A polynomial kernel was employed to allow for "bending" of boundaries, and tuning parameters were optimized using a training dataset. 70% of each dataset was used as training data, and the rest of the 30% was test data.

Conkesta Experiment:

756 samples of soybean, 300 seeds per sample, were ground and DNA extracted. There were three different seed grinds per bin (63 total) and three different DNA extractions per grind (189 total). DNA was purified on Sbeadex, and Palm Taq enzyme was used on a QuantStudio 7 qPCR machine. Nine qPCR reactions were run (1701 total). The test was repeated three times, each on a separate instrument, to determine repeatability.

The probe specific for the Conkesta trait was labeled with FAM dye and the probe for the wild type allele with VIC dye. The emission spectra for FAM and VIC peak at 517 nm (in the blue region of the visible spectrum) and 551 nm (in the green region) respectively, which was detected and distinguished by the PCR instrument.

Enlist Experiment:

21 bins of 300 seeds each were created to test for fractional abundance at 5% increments of detection between 0 and 100%. Each bin of 300 seeds was ground and DNA was extracted. DNA was purified on Sbeadex, and Palm Taq enzyme was used on a QuantStudio 7 qPCR machine. Thirty six qPCR reactions were run (756 reactions total).

Figure 14:
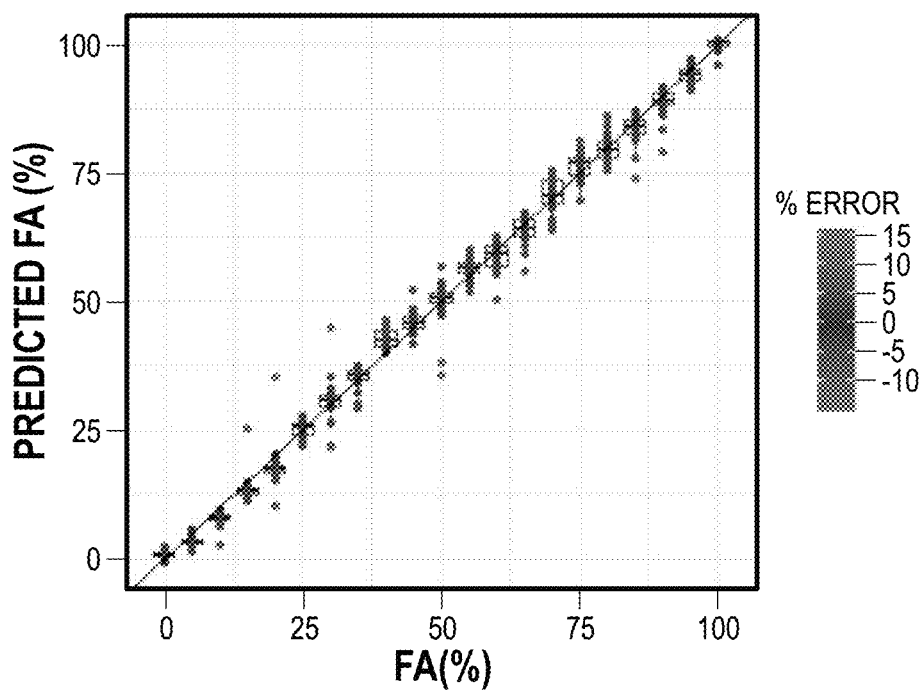
FIG. 14 is a plot showing a distribution of prediction error (Predicted Fractional Abundance (FA) (%) is represented on the y-axis and FA (%) is represented on the x-axis).

Results:

Test accuracy within a 5% margin of error was confirmed, and the assessed algorithms provided fractional abundance with a very high percent of accuracy. Table 3 shows accuracy for each dataset with the SVM algorithm and with a logistic regression algorithm. Results from each algorithm used also show that prediction to be relatively precise. See FIG. 14.

TABLE 3

| Datasets | SVM algorithm | logistic algorithm |
| --- | --- | --- |
| Conkesta Sept 2nd | 92% | 72% |
| Conkesta Sept. 17th | 91% | 79% |
| Enlist | 95% | 95% |

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of processing a grain sample to detect the fractional abundance of a transgenic trait, comprising:
    Grinding and mixing the grain sample,
    Extracting and purifying DNA from the grain sample,
    Running said purified DNA sample in a qPCR reaction, said qPCR reaction comprising at least two different fluorescent probes that competitively bind to the same DNA locus, wherein said DNA locus is indicative of the presence or absence of a transgenic trait,
    Generating results of the qPCR reaction that characterize the competitive binding levels of each of the at least two different fluorescent probes during each cycle of the qPCR reaction, and Interpreting said results with one or more of a machine learning model, ratiometric regression algorithm, or best fit model to determine the fractional abundance of the transgenic trait.

2. The method of claim 1, wherein the results of the qPCR reaction that characterize the competitive binding levels of each of the at least two different fluorescent probes during each cycle of the qPCR reaction are at least one of a standard curve or an N-dimensional curve.

3. The method of claim 1, wherein a machine learning model is used, and the machine learning model has been trained on a range of grain samples comprising levels from 0-100% of transgenic grain in increments of 30% less.

4. The method of claim 1, wherein a machine learning model is used, and the machine learning model has been trained on a range of grain samples comprising levels from 0-100% of transgenic grain in 10% increments.

5. The method of claim 1, wherein a machine learning model is used, and the machine learning model has been trained on a range of grain samples comprising levels from 0-100% of transgenic grain in 5% increments.

6. The method of claim 5, wherein the machine learning model is a support vector machine model.

7. The method of claim 3, wherein the results of the qPCR reaction input into the support vector machine model comprise the ratio of the fluorescence values of FAM/(FAM+VIC).

8. The method of claim 1, wherein the transgenic trait is glyphosate resistance, and the method identifies the genetic sequence that confers glyphosate resistance.

9. The method of claim 1, wherein the at least two different fluorescent probes are FAM and VIC.

10. The method of claim 9, wherein the results of the qPCR reaction input into the support vector machine model comprise the ratio of the fluorescence values of FAM/(FAM+VIC).

11. The method of claim 1, wherein the time elapsed from processing the grain sample to detecting the fractional abundance of the transgenic trait is 15 minutes or less.

12. The method of claim 1, wherein the grain is soybean, corn, sunflower, wheat or canola.

* * * * *